United States Patent
Longo

(10) Patent No.: US 11,883,415 B2
(45) Date of Patent: *Jan. 30, 2024

(54) HIGH CONCENTRATION FORMULATION

(71) Applicant: Cassiopea S.P.A., Lainate (IT)

(72) Inventor: Luigi Maria Longo, Figino Serenza (IT)

(73) Assignee: Cassiopea S.P.A., Lainate (IT)

( * ) Notice: Subject to any disclaimer, the term of this patent is extended or adjusted under 35 U.S.C. 154(b) by 66 days.

This patent is subject to a terminal disclaimer.

(21) Appl. No.: 17/456,218

(22) Filed: Nov. 23, 2021

(65) Prior Publication Data
US 2022/0193093 A1 Jun. 23, 2022

Related U.S. Application Data

(63) Continuation of application No. 16/828,727, filed on Mar. 24, 2020, now Pat. No. 11,213,531, which is a (Continued)

(30) Foreign Application Priority Data

Jun. 25, 2015 (EP) .................... 15173860

(51) Int. Cl.
*A61K 31/573* (2006.01)
*A61K 9/14* (2006.01)
(Continued)

(52) U.S. Cl.
CPC .......... *A61K 31/573* (2013.01); *A61K 9/0014* (2013.01); *A61K 9/06* (2013.01); *A61K 9/08* (2013.01); *A61K 47/10* (2013.01); *A61K 47/22* (2013.01); *A61K 47/26* (2013.01); *A61P 1/00* (2018.01); *A61P 17/14* (2018.01)

(58) Field of Classification Search
CPC ...... A61K 31/573; A61K 47/10; A61K 47/22; A61K 9/14; A61K 9/06; A61K 9/08; A61P 17/10; A61P 17/14
See application file for complete search history.

(56) References Cited

U.S. PATENT DOCUMENTS 2,985,650 A 5/1961 Batres et al.
3,152,154 A 10/1964 Ercoli et al.
(Continued)

FOREIGN PATENT DOCUMENTS

AU 729928 B2 2/2001
CA 2562801 C 9/2010
(Continued)

OTHER PUBLICATIONS

Duarte de Sousa "Novel pharmacological approach for treatment of acne vulgaris," Expert Opinion on Investigational Drugs, 2014, vol. 23, No. 10, pp. 1389-1410 (Year: 2014).*
(Continued)

*Primary Examiner* — Shengjun Wang
(74) *Attorney, Agent, or Firm* — Sterne, Kessler, Goldstein & Fox P.L.L.C.

(57) ABSTRACT

The present disclosure provides high concentration formulations of cortexolone-17α-propionate suitable for treating alopecia.

18 Claims, 2 Drawing Sheets

Related U.S. Application Data continuation of application No. 16/400,262, filed on May 1, 2019, now abandoned, which is a continuation of application No. 15/738,151, filed as application No. PCT/IB2016/053662 on Jun. 20, 2016, now Pat. No. 10,603,327.

(60) Provisional application No. 62/182,988, filed on Jun. 22, 2015.

(51) Int. Cl.

| | | |
|---|---|---|
| A61P 17/14 | (2006.01) | |
| A61K 9/00 | (2006.01) | |
| A61K 47/10 | (2017.01) | |
| A61K 9/08 | (2006.01) | |
| A61K 9/06 | (2006.01) | |
| A61P 1/00 | (2006.01) | |
| A61K 47/22 | (2006.01) | |
| A61K 47/26 | (2006.01) | |

(56) References Cited

U.S. PATENT DOCUMENTS

| | | | |
|---|---|---|---|
| 3,431,173 | A | 3/1969 | Van Der Waard et al. |
| 3,530,038 | A | 9/1970 | De Flines et al. |
| 3,733,318 | A | 5/1973 | Marx |
| 3,780,177 | A | 12/1973 | Ercoli et al. |
| 4,645,763 | A | 2/1987 | Annen et al. |
| 4,670,427 | A | 6/1987 | Annen et al. |
| 5,264,428 | A | 11/1993 | Streber |
| 6,028,208 | A | 2/2000 | Gao et al. |
| 7,169,809 | B2 | 1/2007 | Berthelette et al. |
| 7,550,451 | B2 | 6/2009 | Hillisch et al. |
| 7,576,128 | B2 | 8/2009 | Hu et al. |
| 8,143,240 | B2 | 3/2012 | Ajani et al. |
| 8,785,427 | B2 | 7/2014 | Ajani et al. |
| 8,809,550 | B2 | 8/2014 | Tong |
| 8,865,690 | B2 | 10/2014 | Ajani et al. |
| 9,211,295 | B2 | 12/2015 | Ajani et al. |
| 9,433,268 | B2 | 9/2016 | Ajani et al. |
| 9,486,458 | B2 | 11/2016 | Ajani et al. |
| 9,895,379 | B2 | 2/2018 | Ajani et al. |
| 10,159,682 | B2 | 12/2018 | Ajani et al. |
| 10,166,245 | B2 | 1/2019 | Ajani et al. |
| 10,603,327 | B2 | 3/2020 | Longo |
| 11,213,531 | B2 * | 1/2022 | Longo ................ A61P 1/00 |
| 2004/0138187 | A1 | 7/2004 | Reading et al. |
| 2005/0026889 | A1 | 2/2005 | Ajani et al. |
| 2005/0227994 | A1 | 10/2005 | Gemba et al. |
| 2011/0092472 | A1 * | 4/2011 | Ajani ................ A61P 5/24 |
| | | | 552/595 |
| 2012/0149671 | A1 | 6/2012 | Ajani et al. |
| 2014/0079686 | A1 | 3/2014 | Barman |
| 2014/0154306 | A1 | 6/2014 | Ajani et al. |
| 2014/0322148 | A1 | 10/2014 | Jackson |
| 2016/0303141 | A1 | 10/2016 | Moro et al. |
| 2016/0324873 | A1 | 11/2016 | Ajani et al. |
| 2016/0326210 | A1 | 11/2016 | Ajani et al. |
| 2018/0050047 | A1 | 2/2018 | Moro et al. |
| 2018/0169113 | A1 | 6/2018 | Longo |
| 2019/0083511 | A1 | 3/2019 | Ajani et al. |
| 2019/0282589 | A1 | 9/2019 | Longo |
| 2019/0374553 | A1 | 12/2019 | Longo |

FOREIGN PATENT DOCUMENTS

| | | |
|---|---|---|
| DE | 196 53 730 A1 | 6/1998 |
| GB | 791771 | 3/1958 |
| IT | MI20132157 A1 | 6/2015 |
| JP | 52-10489 A | 1/1977 |
| JP | 59-106500 A | 6/1984 |
| JP | 60-161998 A | 8/1985 |
| JP | 2004-530703 A | 10/2004 |
| JP | 2005-504762 A | 2/2005 |
| JP | 2005-539016 A | 12/2005 |
| JP | 2007522199 A | 8/2007 |
| JP | 2007532634 A | 11/2007 |
| JP | 2013504522 A | 2/2013 |
| WO | WO88/09337 A1 | 12/1988 |
| WO | WO 02/094843 A1 | 11/2002 |
| WO | WO 03/014141 A1 | 2/2003 |
| WO | WO 03/080042 A1 | 10/2003 |
| WO | WO 2004/014935 A1 | 2/2004 |
| WO | WO 2004/060347 A2 | 7/2004 |
| WO | WO 2005/004917 A2 | 1/2005 |
| WO | WO 2006/121097 A1 | 11/2006 |
| WO | WO 2007/014927 A2 | 2/2007 |
| WO | WO 2007/031349 A1 | 3/2007 |
| WO | WO-2009019138 A2 | 2/2009 |

OTHER PUBLICATIONS

Celasco, G., et al., "Biological Profile of Cortexolone 17α-Propionate (CB-03-01), a New Topical and Peripherally Selective Androgen Antagonist," *Arzneimittel—Forschung/Drug. Res.* 54(12):881-886, ECV Editio Cantor Verlag, Germany (2004).

Trifu, V., et al., "Cortexolone 17α-propionate 1% cream, a new potent antiandrogen for topical treatment of acne vulgaris. A pilot randomized, double-blind comparative study vs. placebo and tretinoin 0•05% cream," *The British Journal of Dermatology* 165(1):177-183, British Association of Dermatologists, United Kingdom (2011).

International Search Report and Written Opinion of the International Searching Authority for International Application No. PCT/IB2016/053662, European Patent Office, Rijswjik, Netherlands, dated Aug. 16, 2016, 14 pages.

Toraldo, G., et al., "Topical androgen antagonism promotes cutaneous wound healing without systemic androgen deprivation by blocking β-catenin nuclear translocation and cross-talk with TGF-β signaling in keratinocytes," *Wound Repair and Regeneration* 20(1):61-73, Wound Healing Society, United States (2012).

Ferraboschi, P., et al., "Lipase-catalyzed preparation of corticosteroid 17α-esters endowed with antiandrogenic activity," *Tetrahedron Letters* 49(31):4610-4612, Elsevier Ltd., England (2008).

Gilliver, S., et al., "Regulatory roles of androgens in cutaneous wound healing," *Thrombosis and Haemostasis* 90:978-985, Schattauer GmbH, Germany (2003).

International Preliminary Report on Patentability for International Application No. PCT/IB2016/053662, The International Bureau of WIPO, Switzerland, dated Dec. 26, 2017, 6 pages.

Annen, K., et al., "17-Pivalate in der Pregnanreihe," *Liebigs Ann. Chem*, 705-711, Wiley-VCH Verlag GmbH & Co. KGaA, Germany (1983).

Baldessari, A., et al., "86. Lipase-Catalysed Regioselective Deacetylation of Androstane Derivatives," *Helvetica Chimica Acta*, 79:999-1004, Verlag Helvetica Chimica Acta, Switzerland (1996).

Bavin, M., "Polymorphism in process development. (crystal structure transformations)" in Chemistry and Industry, accessed at https://www.highbeam.com/doc/1G1-7901419.html, accessed on Nov. 17, 2016, *Society of Chemical Industry*, United States, 5 pages (1989).

Belieu, R.M., "Mastodynia," Obstetrics and Gynecology Clinics of North America 21(3):461-477, W.B. Saunders Company, United States (1994).

Biollaz, von M. and Kalvoda, J., "263. Reaktionen von Steroiden mit Dialkylaminoschwefeltrifluoriden. I. 11β-Hydroxysteroide." Helvetica Chimica Acta 60(8):2703-2710, Schweizerische Chemische Gesellschaft, Switzerland (1977).

Bruttomesso, A.C. and Baldessari, A., "Lipase-catalysed deacetylation of androstane and pregnane derivatives: influence of ring D substitution," Journal of Molecular Catalysis B: Enzymatic 29:149-153, Elsevier B.V., Netherlands (2004).

Byrn, S., et al., "Pharmaceutical Solids: A Strategic Approach to Regulatory Considerations," Pharmaceutical Research 12(7):945-954, Plenum Publishing Company, United States (1995).

Caira, M.R., "Crystalline Polymorphism of Organic Compounds," Topics in Current Chemistry, vol. 198, de Meijere, A., et al., Eds., pp. 164-208, Springer-Verlag, Germany (1998).

(56) References Cited

OTHER PUBLICATIONS

Cheung, Y.W., et al., "Resistance to enzymatic hydrolysis as a parameter in drug potency," International Journal of Pharmaceuticals 27:325-333, Elsevier Science Publishers B.V., Netherlands (1985).
Final Office Action, dated Apr. 13, 2007 for U.S. Appl. No. 10/486,386, filed Sep. 16, 2004.
Final Office Action, dated Mar. 21, 2008 for U.S. Appl. No. 10/486,386, filed Sep. 16, 2004.
Final Office Action, dated Feb. 27, 2009 for U.S. Appl. No. 10/486,386, filed Sep. 16, 2004.
Final Office Action, dated May 10, 2018 for U.S. Appl. No. 15/211,087, filed Jul. 15, 2016.
Ford, J.L. and Timmins, P., Eds., "Ch. 6 Thermal analysis in the characterization of pharmaceutical solids," in Pharmaceutical Thermal Analysis: Techniques and Applications, pp. 139-140, Ellis Horwood Limited, England (1989).
Franssen, M.C.R., et al., "Enzymatic Alcoholysis of Alkoxymethyl Alkanoates: a Possible Approach for the Kinetic Resolution of Tertiary Alcohols," Tetrahedron Letters 39:8345-8348, Elsevier Science Ltd., England (1998).
Gardi, R., et al., "52. Derivati di condensazione nella catena laterale di corticosteroidi.—Nota III. Preparazione e reazioni dei 17-monesteri," Gazz. Chim. It. 93:431-450, Palermo, Italy (1963).
Gardi, R., et al., "Corticosteroid 17α-Monoesters from 17α,21-Cyclic Orthoesters," Tetrahedron Letters, 13:448-451, Pergamon Press Ltd., Great Britain (1961).
Hilfiker, R., Ed., "Characterization of Polymorphic Systems Using Thermal Analysis," in Polymorphisms in the Pharmaceutical Industry, pp. 46-48, Wiley-VCH Verlag GmbH & Co. KGaA, Germany (2006).
Japanese Office Action for Application No. 2010-518628 dated Feb. 8, 2013.
Meriggiola, M.C. and Pelusi, G., "Advances in male hormonal contraception," Expert Opin. Investig. Drugs 15(4):389-397, Ashley Publications, England (2006).
Misaki, T., et al., "Enzymic hydrolysis of hydrocortisone diesters in skin," Yakuzaigaku 42(2):92-98, Abstract, CAPLUS Chemical Abstract Database Accession No. 575431 (1982).
Morrison, R.T. and Boyd, R.N., Eds., "Chap. 20 Functional Derivatives of Carboxylic Acids," in Organic Chemistry, Sixth Edition, pp. 764-766, Prentice-Hall, Inc., Englewood Cliffs, New Jersey, United States (1992).
Non-Final Office Action, dated Sep. 25, 2006 for U.S. Appl. No. 10/486,386, filed Sep. 16, 2004.
Non-Final Office Action, dated Sep. 7, 2007 for U.S. Appl. No. 10/486,386, filed Sep. 16, 2004.
Non-Final Office Action, dated Jul. 10, 2008 for U.S. Appl. No. 10/486,386, filed Sep. 16, 2004.
Non-Final Office Action, dated Jul. 13, 2011 for U.S. Appl. No. 12/457,870, filed Jun. 24, 2009.
Notice of Allowance, dated Nov. 16, 2011 for U.S. Appl. No. 12/457,870, filed Jun. 24, 2009.
Non-Final Office Action, dated Dec. 28, 2012 for U.S. Appl. No. 12/671,932, filed Aug. 12, 2010.
Notice of Allowance, dated Apr. 14, 2014 for U.S. Appl. No. 12/671,932, filed Aug. 12, 2010.
Non-Final Office Action, dated Apr. 24, 2014 for U.S. Appl. No. 14/103,707, filed Dec. 11, 2013.
Notice of Allowance, dated Jul. 17, 2014 for U.S. Appl. No. 14/103,707, filed Dec. 11, 2013.
Non-Final Office Action, dated May 11, 2015 for U.S. Appl. No. 14/550,559, filed Nov. 21, 2014.
Notice of Allowance, dated Sep. 23, 2015 for U.S. Appl. No. 14/474,765, filed Sep. 2, 2014.
Non-Final Office Action, dated Nov. 25, 2015 for U.S. Appl. No. 14/073,928, filed Nov. 7, 2013.
Non-Final Office Action, dated Jan. 20, 2016 for U.S. Appl. No. 14/886,774, filed Oct. 19, 2015.

Notice of Allowance, dated May 4, 2016 for U.S. Appl. No. 14/073,928, filed Nov. 7, 2013.
Notice of Allowance, dated Jun. 30, 2016 for U.S. Appl. No. 14/886,774, filed Oct. 19, 2015.
Notice of Allowance, dated Oct. 18, 2017 for U.S. Appl. No. 14/885,488, filed Oct. 16, 2015.
Non-Final Office Action, dated Nov. 20, 2017 for U.S. Appl. No. 15/211,094, filed Jul. 15, 2016.
Non-Final Office Action, dated Nov. 28, 2017 for U.S. Appl. No. 15/211,087, filed Jul. 15, 2016.
Final Office Action, dated May 3, 2018 for U.S. Appl. No. 15/211,094, filed Jul. 15, 2016.
Notice of Allowance, dated Aug. 9, 2018 for U.S. Appl. No. 15/211,094, filed Jul. 15, 2016.
Notice of Allowance, dated Aug. 24, 2018 for U.S. Appl. No. 15/211,087, filed Jul. 15, 2016.
Schinzer, W.C., et al., "Characterization and Interconversion of Polymorphs of Premafloxacin, a New Quinolone Antibiotic," Journal of Pharmaceutical Sciences 86(12):1426-1431, American Chemical Society and American Pharmaceutical Association, United States (1997).
Tuladhar, M.D., et al., "Thermal behaviour and dissolution properties of phenylbutazone polymorphs," J. Pharm. Pharmcol. 35:208-214, Pharmaceutical Society of Great Britain, England (1983).
Turner, R.B., "Acylation of 17-Hydroxy-20-ketosteroids," J. Am. Chem. Soc.75:3489-3492, American Chemical Society, United States (1953).
Voigt, W. and Hsia, S.L., "The Antiandrogenic Action of 4-Androsten-3-one-17β-Carboxylic Acid and Its Methyl Ester on Hamster Flank Organ," Endocrinology 92(4):1216-1222, Endocrine Society, United States (1973).
Anderson, B. D. and Taphouse, V., "Initial Rate Studies of Hydrolysis and Acyl Migration in Methylprednisolone 21-Hemisuccinate and 17-Hemisuccinate," Journal of Pharmaceutical Sciences 70(2):181-186, American Pharmaceutical Association, United States (1981).
Clinical trials data published on Oct. 31, 2014, retrieved from https://clinicaltrials.gov/ct2/history/NCT02279823?V_1=View#studypagetop, 7 pages.
Cosmo Pharmaceuticals S.p.A. Reports Exciting Results in P.O.C. Alopecia Study, published on Oct. 6, 2010, retrieved from https://www.biospace.com/article/releases/cosmo-pharmaceuticals-s-p-a-reports-exciting-results-in-p-o-c-alopecia-study-/, 4 pages.
Blagden, N., et al., "Crystal engineering of active pharmaceutical ingredients to improve solubility and dissolution rates," Advanced Drug Delivery Reviews 56:617-630, Elsevier B.V., Netherlands (2007).
Morissette, S. L., et al., "High-throughput crystallization: polymorphs, salts, co-crystals and solvates of pharmaceutical solids," Advanced Drug Delivery Reviews 56:275-300, Elsevier B.V., Netherlands (2004).
Vishweshwar, P., et al., "Pharmaceutical Co-Crystals," Journal of Pharmaceutical Sciences 95(3):499-516, Wiley-Liss, Inc. and the American Pharmacists Association, United States (2006).
Khankari, R. K., et al., "Pharmaceutical hydrates," Thermochimica Acta 248:61-79, Elsevier B.V., Netherlands (1995).
Non-Final Office Action dated Oct. 19, 2018 for U.S. Appl. No. 15/738,151, having a 371(c) date of Dec. 20, 2017.
Notice of Allowance dated May 17, 2019 for U.S. Appl. No. 15/738,151, having a 371(c) date of Dec. 20, 2017.
Notice of Allowance dated Oct. 17, 2019 for U.S. Appl. No. 15/738,151, having a 371(c) date of Dec. 20, 2017.
Non-Final Office Action dated Oct. 2, 2019 for U.S. Appl. No. 16/195,083, filed Nov. 19, 2018.
Redmond, G., "Female Hair Loss (Alopecia)," accessible at https://www.hormonehelpny.com/column/alopecia.htm, The Service of the Hormone Center of New York, p. 1-11 (Mar. 23, 2008).
Bolotnaya; L.A.. "Treatment of androgenetic alopecia from position of evidence-based medicine," Kharkov Medical Academy of Postgraduate Education 4(58):9-10, (2012).
Bolotnaya; L.A.. "Treatment of androgenetic alopecia from position of evidence-based medicine," Kharkov Medical Academy of Postgraduate Education 4(58):9-10, (2012) English Translation.

(56) References Cited

OTHER PUBLICATIONS

Shin et al., "Interpretation of animal dose and human equivalent dose for Drug Development," The Journal of Korean Oriental Medicine. 2010, vol. 31, No. 3, pp. 1-7 (Year: 2010).
Notice of Allowance dated Jul. 25, 2019 for U.S. Appl. No. 15/738,151, having a 371 (c) date of Dec. 20, 2017.
Notice of Allowance dated Dec. 13, 2019 for U.S. Appl. No. 15/738,151, having a 371 (c) date of Dec. 20, 2017.
Notice of Allowance dated Mar. 3, 2020 for U.S. Appl. No. 15/738,151, having a 371 (c) date of Dec. 20, 2017.
Non-Final Office Action dated Jul. 25, 2019 for U.S. Appl. No. 16/400,262, filed May 1, 2019.
Final Office Action dated Dec. 17, 2019 for U.S. Appl. No. 16/400,262, filed May 1, 2019.
Third Party Submission dated Oct. 17, 2019, mailed Oct. 22, 2019 for U.S. Appl. No. 16/400,262, filed May 1, 2019 (21 pages).
Xuejun, Z., et al., "Dermatovenerology," 1$^{st}$ Edition, Beijing Medical University and Beijing Union Medical University, China (Sep. 1995).
Biospace, "Cosmo Pharmaceuticals S.p.A. Reports Exciting Results in P.O.C. Alopecia Study," retrieved from https://www.biospace.com/article/relesases/cosmo-pharmaceuticals-s-p-a-reports-exciting-reults-in-p-o-c-alopecia-study-/, published Oct. 6, 2010, retrieved on Dec. 17, 2019, 4 pages.
Cosmo Pharmaceuticals, "R&D Day," Presented Dec. 1, 2010, Zuerich, Switzerland, 88 pages.
Cosmo Pharmaceuticals, "R&D Day," Presented Jan. 25, 2013, Lainate, Italy, 67 pages.
Osborne, D.W., et al., "Diethylene glycol monethyl ether: an emerging solvent in topical dermatology products," Journal of Cosmetic Dermatology 10:324-329, Wiley Periodicals, United States (2011).
Sullivan, D.W., et al., "A review of the nonclinical safety of Transcutol®, a highly purified form of diethylene glycol monoethyl ether (DEGEE) used as a pharmaceutical excipient," Food and Chemical Toxicology 72:40-50, Elsevier, Netherlands (2014).

* cited by examiner

HIGH CONCENTRATION FORMULATION

BACKGROUND

Alopecia is a group of disorders with multiple and varying etiologies that results in hair loss from the body. The most common form of alopecia is androgenetic alopecia ("AGA"). AGA is also commonly called alopecia androgenetica, male pattern baldness, or male-pattern or female-pattern hair loss. It has been reported that AGA affects roughly 50% of men over 40. This form of alopecia may eventually affect up to 80% of white men by the age of 70 and about half of all women. Hair loss is often a cause of great concern to a patient for cosmetic and psychological reasons, but it can also be an important sign of systemic disease.

AGA is a hereditary hair follicle disease that is also androgen-dependent. Dihydrotestosterone, in particular, plays a major role in the development and progression of AGA. Hair loss with AGA is progressive such that patients with disease experience a reduction in the normal 4:1 terminal-to-vellus hair ratio over a period of time. During this process, terminal hairs are converted to indeterminate hairs and finally into vellus hairs. Men present with hair thinning in the temporal areas, which advances to the crown (vertex) area as the AGA progresses. Women usually have more diffuse thinning on the crown area, and less commonly present with a male-type pattern.

In vivo, AGA is characterized by increased levels and activity of 5α-reductase isoenzymes. These enzymes convert testosterone (T) into its active metabolite dihydrotestosterone (DHT). High concentrations of DHT at the hair-follicle level, due to increased binding capacity of the hormone to hair-follicle androgen receptors, shorten the hair cycle and gradually miniaturize scalp follicles. Following miniaturization of the follicles, fibrous tracts remain. These DHT-dependent effects are considered, in most cases, reversible, such that AGA may be susceptible to medical treatment with drugs able to reduce DHT production, or to antagonize DHT/T interaction with hair-follicle androgen receptors.

Current medical management of AGA comprises surgical and pharmacological treatment options. The most common form of surgical intervention for AGA is hair transplantation. This procedure has been performed successfully for the past four decades. Hair transplantation involves harvesting intact hair follicles from within a safe donor area (SDA) of a patient's scalp by either follicular unit strip surgery (FUSS) or follicular unit extraction (FUE). Refinements to these procedures over the last decade have led to markedly improved hair survival and more natural appearing results.

Although cosmetic results after surgery are often satisfactory, surgery can only be performed when a sufficient quantity of donor plugs (or follicles) are available to cover the balding area(s). Additionally, hair transplantation is generally reserved for patients who have experienced massive hair loss and for patients in whom AGA is not still evolving. In younger patients, for example, hair transplantation is generally not recommended because androgens, particularly DHT, can act on the newly transplanted follicles resulting in same thinning and eventual hair loss that affected the originally present follicles. For this reason, at the initial onset and in the initial phases of the AGA, pharmacological intervention is preferred.

Currently, only two medicinal products are approved for treatment of AGA: minoxidil (sold commercially as ROGAINE® and its generic forms) and finasteride (sold commercially as PROPECIA®). Minoxidil, which is formulated as a topical drug product, is currently available at two strength levels—2% (topical solution) and 5% (as a topical solution or foam). To exert its effect minoxidil needs to be transformed into its active metabolite, minoxidil sulfate, by the enzyme sulfotransferase. This enzyme is present in the outer root sheath of anagen follicles.

Although the exact mechanism by which minoxidil promotes hair growth is still unclear, it is believed that minoxidil sulfate opens ATP-sensitive potassium channels in cell membranes resulting in vasodilation. Vasodilation, however, does not appear to be responsible for minoxidil-induced hair growth. Other possible effects of minoxidil on hair follicles include: a) increased expression of vascular endothelial growth factor (VEGF) mRNA in the dermal papilla, which indicates that the drug induces angiogenesis in the dermal papilla; b) activation of cytoprotective prostaglandin synthase-1, a cytoprotective enzyme that stimulates hair growth; and c) increased expression of hepatocyte growth factor (HGF), which is an hair growth promoter.

In various clinical trials, minoxidil was found to be effective in significantly improving total hair count and non-vellus hair count after 6 to 12 months of treatment, in comparison to placebo. Moreover, minoxidil preparations are well tolerated, with only mild side effects. Despite these beneficial effects, minoxidil does not reduce dihydrotestosterone (DHT) or the enzyme responsible for its accumulation around the hair follicle, 5-alpha reductase—the primary mediator of male pattern baldness in genetically susceptible individuals. As a result, when treatment is stopped, DHT shrinks and ultimately destroys genetically predisposed hair follicles.

Finasteride, on the other hand, inhibits 5-alpha reductase type II, which is responsible for transforming testosterone into DHT at the follicle. Finasteride is administered orally in a 1 mg tablet formulation. A single oral administration of finasteride 1 mg decreases serum DHT as well as scalp DHT up to 70% compared to baseline. In several published clinical trials, finasteride 1 mg was found to be effective in significantly improving the total hair count in comparison to placebo after 6 months of treatment. The significant increase in total hair counts, in comparison to placebo, in patients under treatment with finasteride 1 mg were maintained in long term treatments (up to 60 months).

Even though finasteride effectively stops hair loss and improves new hair growth, there are possible adverse effects associated with its use. Foremost, finasteride is contraindicated in women due to suspected teratogenic effects. Thus, women who are or may become pregnant, regardless of whether they suffer from AGA, are strongly cautioned to avoid contact with broken or crushed tablets. Additionally, because finasteride is distributed systemically, it not only reduces DHT levels at the hair follicle, but in the plasma as well. This systemic activity is responsible for finasteride's main side effects, which include decreased libido, erectile dysfunction (impotence), ejaculation disorders, and decreased volume of ejaculate. Other less common side effects include breast swelling, palpitations, pain in testicles, persistent decrease in sex drive after discontinuation, infertility, and depression.

In view of the deficiencies and drawbacks associated with finasteride and minoxidil therapies, it is apparent that there is a need in the art for new methods and active agents for treating alopecia, and in particular, AGA.

BRIEF SUMMARY

Cortexolone-17α-propionate (17α-propionyloxy-21-hydroxy-pregna-4-ene-3,20-dione) is a known topical antiandrogen that displaces androgenic hormones from binding with their receptors. It is known to be suitable for treating acne, alopecia, and other diseases of skin and cutaneous appendages. See, e.g., U.S. Pat. Nos. 8,143,240 and 8,865,690. The compound is also known to exist in several distinct crystalline polymorphs, each having unique properties. See, e.g., U.S. Pat. No. 8,785,427. Each of these patents is incorporated herein by reference in its entirety.

Although certain formulations of cortexolone-17α-propionate have been disclosed in the art, these formulations were limited to a concentration of less than 2% by weight due to inherent solubility limitations of the active and concerns that the administration of higher concentrations could lead to greater and unwanted systemic exposure to the active and/or its metabolites—particularly after repeated administration.

Despite these concerns, it has now been unexpectedly discovered that it is possible to prepare pharmaceutical formulations comprising cortexolone-17α-propionate as the therapeutic agent for topical administration at concentrations of greater than 2% by weight. These pharmaceutical formulations have favorable characteristics for the treatment of alopecia and provide optimal topical delivery of the therapeutic agent as evidenced by the pharmacokinetic profiles described herein. In particular, these pharmacokinetic profiles show that the formulations described herein advantageously maximize topical delivery of cortexolone-17α-propionate in the skin and/or in the scalp while simultaneously minimizing systemic exposure to cortexolone-17α-propionate or any of its metabolites. As a result of such drug disposition, an advantageous clinical result can be realized after daily topical administration for an appropriate amount of time, such as a few days, weeks, or months. Moreover, it has also been discovered that the pharmaceutical formulations described herein possess favorable stability profiles, allowing for finished product storage at room temperature for at least two years.

In certain embodiments the present disclosure provides a method of treating alopecia in a patient in need thereof, comprising topically administering to the patient a pharmaceutical formulation comprising at least 2.1 weight percent cortexolone-17α-propionate and one or more pharmaceutically acceptable solvents.

In certain embodiments, the pharmaceutical formulation comprises from about 2.1 weight percent to about 20 weight percent cortexolone-17α-propionate. In other embodiments, the pharmaceutical formulation comprises from about 2.1 weight percent to about 17 weight percent cortexolone-17α-propionate. In other embodiments, the pharmaceutical formulation comprises from about 2.5 weight percent to about 17 weight percent cortexolone-17α-propionate. In other embodiments, the pharmaceutical composition comprises from about 2.5 weight percent to 15 weight percent cortexolone-17α-propionate. In other embodiment, the pharmaceutical composition comprises from about 3 weight percent to about 15 weight percent cortexolone-17α-propionate. In other embodiments, the pharmaceutical formulation comprises about 6 weight percent cortexolone-17α-propionate. In other embodiments, the pharmaceutical formulation comprises about 7 weight percent cortexolone-17α-propionate. In other embodiments, the pharmaceutical formulation comprises about 7.5 weight percent cortexolone-17α-propionate. In other embodiments, the pharmaceutical formulation comprises about 8 weight percent cortexolone-17α-propionate. In other embodiments, the pharmaceutical formulation comprises about 9 weight percent cortexolone-17α-propionate. In other embodiments, the pharmaceutical formulation comprises about 10 weight percent cortexolone-17α-propionate. In other embodiments, the pharmaceutical formulation comprises about 11 weight percent cortexolone-17α-propionate. In other embodiments, the pharmaceutical formulation comprises about 12 weight percent cortexolone-17α-propionate. In other embodiments, the pharmaceutical formulation comprises about 13 weight percent cortexolone-17α-propionate. In other embodiments, the pharmaceutical formulation comprises about 14 weight percent cortexolone-17α-propionate. In other embodiments, the pharmaceutical formulation comprises about 15 weight percent cortexolone-17α-propionate.

In certain embodiments, the pharmaceutical formulation comprises from about 2.1 weight percent to about 5.5 weight percent cortexolone-17α-propionate. In other embodiments, the pharmaceutical formulation comprises about 2.5 weight percent cortexolone-17α-propionate. In other embodiments, the pharmaceutical formulation comprises about 3 weight percent cortexolone-17α-propionate. In other embodiments, the pharmaceutical formulation comprises about 4 weight percent cortexolone-17α-propionate. In still other embodiments, the pharmaceutical formulation comprises about 5 weight percent cortexolone-17α-propionate. In still further embodiments, the pharmaceutical formulation comprises about 5.5 weight percent cortexolone-17α-propionate. In yet another embodiment, the pharmaceutical formulation comprises 5 weight percent cortexolone-17α-propionate.

In certain embodiments, the pharmaceutical formulation is a liquid or semi-solid formulation. In a further embodiment, the pharmaceutical formulation is a solution, a suspension, an emulsion, a microemulsion, a cream, a gel, a foam, or an ointment.

In certain embodiments, the pharmaceutical formulation is anhydrous and contains less than about 5 weight percent water. In further embodiments, the pharmaceutical formulation is a solution.

In certain embodiments, the formulation provides a mean $C_{max}$ of cortexolone-17α-propionate of about 0.5 to about 3 ng/ml after topical application of a single dose. In certain embodiments, the mean $C_{max}$ of cortexolone-17α-propionate after administration of a single topical dose is about 0.5 to about 1.5 ng/ml. In other embodiments, the mean $C_{max}$ of cortexolone-17α-propionate after administration of a single topical dose is 1.04±0.41 ng/ml.

In still other embodiments, the formulation provides a mean $C_{max}$ of cortexolone-17α-propionate of less than about 3 ng/ml after topical application of a single dose comprising about 50 mg of cortexolone-17α-propionate.

In some embodiments, the formulation provides a mean $T_{max}$ of cortexolone-17α-propionate of less than about 20 hours after administration of a single topical dose. In other embodiments, the formulation provides a mean $T_{max}$ of cortexolone-17α-propionate of less than about 15 hours after administration of a single topical dose. In yet another embodiment, the formulation provides a mean $T_{max}$ of cortexolone-17α-propionate of less than about 12 hours after administration of a single topical dose. And in yet another embodiment, the formulation provides a mean $T_{max}$ of cortexolone-17α-propionate of about 6.22±5.17 hours after topical administration of a single dose comprising about 50 mg of cortexolone-17α-propionate.

In certain embodiments, the formulation provides a mean $AUC_{0-t}$ of less than about 25 (ng*h)/ml after topical administration of a single dose comprising about 50 mg of cortexolone-17α-propionate. In other embodiments, the formulation provides a mean $AUC_{0-t}$ of less than about 20 (ng*h)/ml after topical administration of a single dose comprising about 50 mg of cortexolone-17α-propionate. And in still other embodiments, the formulation provides a mean $AUC_{0-t}$ of about 15.69±4.3 (ng*h)/ml after topical administration of a single dose comprising about 50 mg of cortexolone-17α-propionate.

In some embodiments, the formulation provides a mean steady-state $C_{max}$ of cortexolone-17α-propionate of about 3.82±1.34 ng/ml after topical administration of a single dose comprising about 50 mg of cortexolone-17α-propionate.

In other embodiments, the formulation provides a mean steady-state $T_{max}$ of cortexolone-17α-propionate of about 4.38±1.96 hours after topical administration of a single dose comprising about 50 mg of cortexolone-17α-propionate.

In some embodiments, the formulation provides a mean steady-state $AUC_{0-t}$ of about 37.37±12.36 (ng*h)/ml after topical administration of a single dose comprising about 50 mg of cortexolone-17α-propionate.

In some embodiments, the formulations of the invention provide a mean change from baseline in Target Area Hair Count equal to or higher than 8 hairs/cm$^2$ after 6 months of daily or BID application.

In some embodiments, the alopecia is androgenetic alopecia, alopecia areata, telogen effluvium, anagen effluvium, traction alopecia, or a combination of any of the foregoing. In certain embodiments, the alopecia areata is selected from the group consisting of diffuse alopecia areata, alopecia areata monolocularis, alopecia areata multilocularis, ophiasis, alopecia totalis, and alopecia universalis.

In some embodiments, the alopecia is androgenetic alopecia.

In some embodiments, the formulation further comprises at least one antioxidant, at least an emulsifier, or a combination of the foregoing.

In some embodiments, the formulation is administered once or twice daily.

In some embodiments, the formulation is a liquid.

In some embodiments, from about 0.2 to about 2.0 ml of the formulation are administered during each application.

In a further embodiment, the present disclosure provides a topical pharmaceutical formulation comprising cortexolone-17α-propionate at a concentration of at least 2.1 weight percent, and one or more pharmaceutically acceptable solvents.

In certain embodiments, the formulation comprises from about 2.1 weight percent to about 20 weight percent cortexolone-17α-propionate. In other embodiments, the formulation comprises from about 2.1 weight percent to about 17 weight percent cortexolone-17α-propionate. In other embodiments, the formulation comprises from about 2.5 weight percent to about 17 weight percent cortexolone-17α-propionate. In other embodiments, the composition comprises from about 2.5 weight percent to 15 weight percent cortexolone-17α-propionate. In other embodiment, the composition comprises from about 3 weight percent to about 15 weight percent cortexolone-17α-propionate. In other embodiments, the formulation comprises about 6 weight percent cortexolone-17α-propionate. In other embodiments, the formulation comprises about 7 weight percent cortexolone-17α-propionate. In other embodiments, the formulation comprises about 7.5 weight percent cortexolone-17α-propionate. In other embodiments, the formulation comprises about 8 weight percent cortexolone-17α-propionate. In other embodiments, the formulation comprises about 9 weight percent cortexolone-17α-propionate. In other embodiments, the formulation comprises about 10 weight percent cortexolone-17α-propionate. In other embodiments, the formulation comprises about 11 weight percent cortexolone-17α-propionate. In other embodiments, the formulation comprises about 12 weight percent cortexolone-17α-propionate. In other embodiments, the formulation comprises about 13 weight percent cortexolone-17α-propionate. In other embodiments, the formulation comprises about 14 weight percent cortexolone-17α-propionate. In other embodiments, the formulation comprises about 15 weight percent cortexolone-17α-propionate.

In certain embodiments, the formulation comprises cortexolone-17α-propionate at a concentration from about 2.1 weight percent to about 5.5 weight percent. In other embodiments, the formulation comprises about 2.5 weight percent cortexolone-17α-propionate. In other embodiments, the topical pharmaceutical formulation comprises about 3 weight percent cortexolone-17α-propionate. In another embodiment, the pharmaceutical formulation comprises about 4 weight percent cortexolone-17α-propionate. In still another embodiment, the pharmaceutical formulation comprises about 5 weight percent cortexolone-17α-propionate. In yet a further embodiment, the pharmaceutical formulation comprises about 5.5 weight percent cortexolone-17α-propionate. And in yet another embodiment, the pharmaceutical formulation comprises 5 weight percent cortexolone-17α-propionate.

In certain embodiments, the pharmaceutical formulation is a liquid or semi-solid formulation. In some embodiments, the liquid or semi-solid, formulation is a solution, a suspension, an emulsion, a microemulsion, a cream, a gel, a foam, or an ointment.

In some embodiments, the pharmaceutical formulation is anhydrous and comprises less than about 5 percent water by weight. In other embodiments, the pharmaceutical formulation is anhydrous and comprises less than about 3 percent water by weight.

In some embodiments, the topical pharmaceutical formulation is a solution.

In some embodiments, the formulation provides a mean steady-state $C_{max}$ of less than about 7.0 ng/ml of cortexolone-17α-propionate upon the application of an amount of the formulation including about 50 mg of cortexolone-17α-propionate.

In other embodiments, the formulation provides a mean steady-state $T_{max}$ of cortexolone-17α-propionate of less than about 8.0 hours, upon the application of an amount of the formulation including about 50 mg of cortexolone-17α-propionate.

In certain embodiments, the formulation provides an $AUC_T$ of cortexolone-17α-propionate of less than about 64.1 (ng*h)/ml, upon the application of an amount of the formulation including about 50 mg of cortexolone-17α-propionate In certain embodiments, the formulation is for use in the treatment of alopecia.

In certain embodiments, the one or more pharmaceutically acceptable solvents are selected from the group consisting of a polyol, a polyol ether, and a $C_1$-$C_7$ alcohol. In some embodiments, the $C_1$-$C_7$ alcohol is ethanol, isopropanol, or methanol. In other embodiments, the $C_1$-$C_7$ alcohol is ethanol. In certain embodiments, the ethanol is 96°. In some embodiments, the ethanol is absolute ethanol.

In some embodiments, the polyol is selected from the group consisting of ethylene glycol, propylene glycol, glycerol, and hexanetriol. In particular embodiments, the polyol is propylene glycol.

In certain embodiments, the polyol ether is selected from the group consisting of polypropylene glycol, polyethylene glycol, polyethylene-polypropylene triblock copolymers, dipropylene glycol, and diethylene glycol monoethyl ether. In particular embodiments, the polyol ether is diethylene glycol monoethyl ether.

In some embodiments, polyol is propylene glycol, the polyol ether is diethylene glycol monoethyl ether, and the $C_1$-$C_7$ alcohol is ethanol.

In certain embodiments, formulation is anhydrous and contains less than 5% water by weight or less than 3% water by weight.

In other embodiments, the formulation further comprises an emulsifier.

In certain embodiments, the formulation further comprises an antioxidant. In some embodiments, the antioxidant is selected from the group consisting of butylated hydroxytoluene (BHT), butylated hydroxyanisole (BHA), ascorbyl palmitate, ascorbic acid, alpha tocopherol, and propyl gallate. In certain embodiments, the antioxidant ascorbyl palmitate.

In certain embodiments, the emulsifier is selected from the group consisting of PEG-15 hydroxystearate (also known as polyoxyl-15-hydroxystearate), PEG-30 stearate, PEG-40 laurate, PEG-40 oleate, polysorbate 20, polysorbate 60, polysorbate 80, PEG-20 cetostearyl ether, polyoxyl 25 cetostearyl, cetomacrogol 1000, sorbitan monolaurate, sorbitan monopalmitate, sorbitan monooleate propylene glycol esters of fatty acids, polyglycerol esters of fatty acids, polyoxyl 5 castor oil, polyoxyl 15 castor oil, polyoxyl 35 castor oil, polyoxyl 40 hydrogenated castor oil, caprylocapryl polyoxyil-8 glycerides; caprylocaproyl polyoxylglycerides, lauroyl polyoxylglycerides, oleoyl polyoxylglycerides, and combinations of any of the foregoing. In certain embodiments, the emulsifier is polysorbate 80.

In another embodiment, the present description provides a method of treating alopecia, the method comprising topically administering to a subject in need thereof a topical pharmaceutical formulation as described herein, wherein twice a day topical administration of the formulation for at least six months achieves hair growth comparable to hair growth observed upon administration of oral finasteride for the same period of time. In one aspect, the method provides a reduced incidence of adverse effects selected from the group consisting of decreased libido, erectile dysfunction (impotence), ejaculation disorders, and decreased volume of ejaculate.

In another embodiment, the present description provides a method of treating alopecia, the method comprising topically administering to a subject in need thereof a topical pharmaceutical formulation as described herein, wherein the topical administration of the formulation for at least six months achieves a mean value of the change from baseline in non-vellus Target Area Hair Count (TAHC) of about 12.7 in comparison with vehicle.

In another embodiment, the present description provides a method of treating alopecia, the method comprising topically administering to a subject in need thereof a topical pharmaceutical formulation as described herein, wherein the topical administration of the formulation for at least six months achieves a weighted average Hair Growth Assessment (HGA) score of about 0.30 in comparison with vehicle.

In another embodiment, the present description provides a method of treating alopecia, the method comprising topically administering to a subject in need thereof a topical pharmaceutical formulations as described herein, wherein the topical administration of the formulation for at least six months achieves a weighted average Investigator's Global Assessment (IGA) score of about 0.43 in comparison with vehicle.

In another embodiment, the present description provides a method of treating alopecia, the method comprising topically administering to a subject in need thereof a topical pharmaceutical formulation as described herein, wherein the topical administration of the formulation for at least six months is free from systemic antiandrogenic side-effects.

In another embodiment, the present description provides a method of treating alopecia, the method comprising topically administering to a subject in need thereof a topical pharmaceutical formulation as described herein, wherein the topical administration of the formulation provides a mean change from baseline in Target Area Hair Count equal to or higher than 9 hairs/cm$^2$ after 6 months of daily or BID application; or a mean change from baseline in Target Area Hair Count equal to or higher than 10 hairs/cm$^2$ after 6 months of daily or BID application; or a mean change from baseline in Target Area Hair Count equal to or higher than 11 hairs/cm$^2$ after 6 months of daily or BID application; or a mean change from baseline in Target Area Hair Count equal to or higher than 12 hairs/cm$^2$ after 6 months of daily or BID application; or a weighted average HGA score equal to or higher than 0.20 after 6 months of daily or BID application; or a weighted average HGA score equal to or higher than 0.30 after 6 months of daily or BID application; or a weighted average HGA score equal to or higher than 0.40 after 6 months of daily or BID application; or a weighted average IGA score equal to or higher than 0.10 after 6 months of daily or BID application; or a weighted average IGA score equal to or higher than 0.20 after 6 months of daily or BID application; or a weighted average IGA score equal to or higher than 0.30 after 6 months of daily or BID application; or a favorable (positive) HGA score in at least about 10% of subjects after 6 months of daily or BID application; or a favorable (positive) HGA score in at least about 20% of subjects after 6 months of daily or BID application; or a favorable (positive) HGA score in at least about 30% of subjects after 6 months of daily or BID application; or a favorable (positive) IGA score in at least about 10% of subjects after 6 months of daily or BID application; or a favorable (positive) IGA score in at least about 20% of subjects after 6 months of daily or BID application; or a favorable (positive) IGA score in at least about 30% of subjects after 6 months of daily or BID application; or a favorable (positive) IGA score in at least about 40% of subjects after 6 months of daily or BID application.

BRIEF DESCRIPTION OF THE DRAWINGS

The foregoing summary, as well as the following detailed description of the embodiments, will be better understood when read in conjunction with the appended figures. For the purpose of illustration, the figures may describe the use of specific embodiments. It should be understood, however, that the compounds, formulations and compositions described herein are not limited to the precise embodiments discussed or described in the figures.

DETAILED DESCRIPTION

Figure 1:
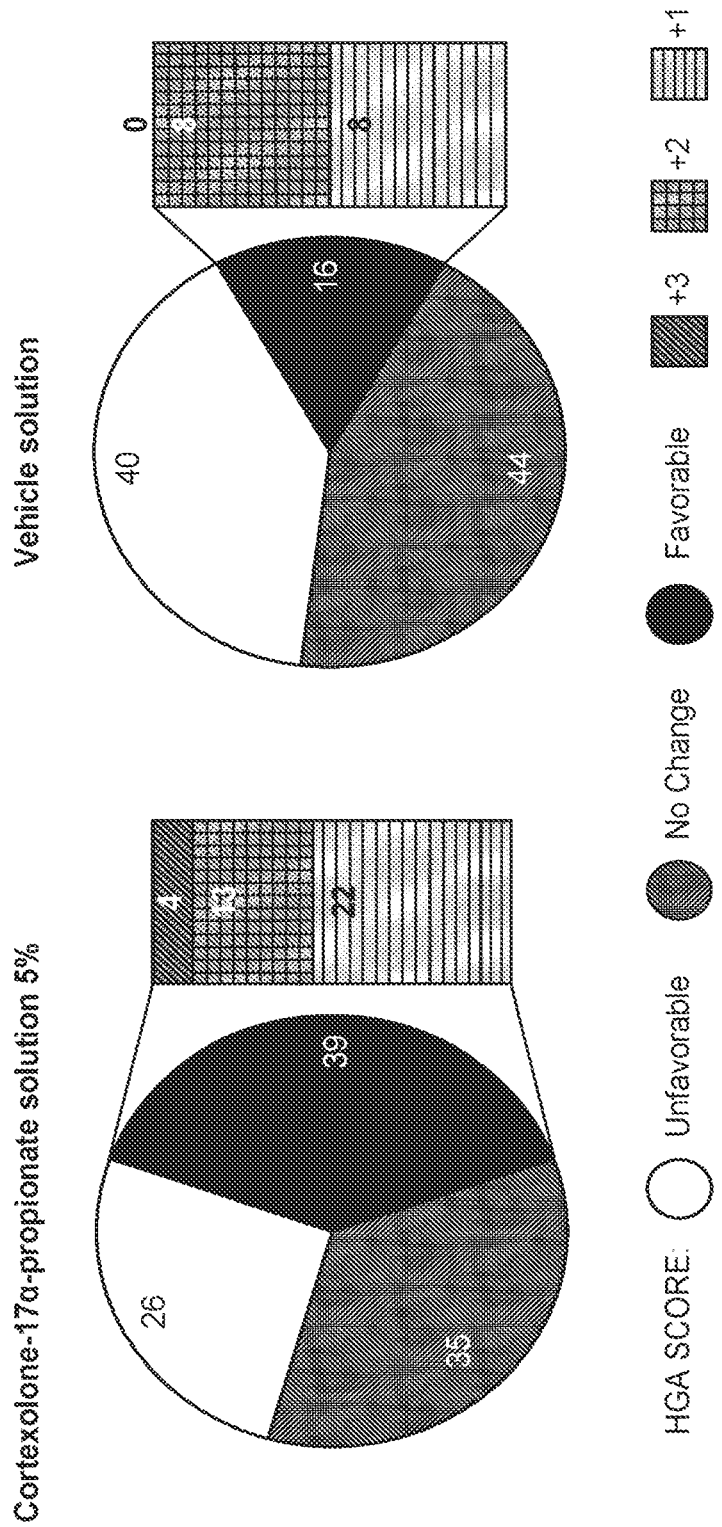
FIG. 1 depicts the frequency distribution of Hair Growth Assessment (HGA), performed by study subjects, in two treatment groups after 6 months of treatment in the Phase 2 clinical study in males with androgenic alopecia (AGA) described in Example 9.

The formulations described herein constitute a major improvement to the currently available therapies of alopecia, and specifically AGA, and would allow the physicians to have an effective, valuable and safe treatment of alopecia, and in particular AGA.

It has been found that the pharmaceutical formulations for topical administration described herein provide an optimal topical delivery of the therapeutic agent cortexolone-17α-propionate and, when used in the treatment of alopecia, and in particular AGA, are able to achieve similar results, in terms of efficacy, as commercially available finasteride 1 mg tablets (PROPECIA®) per os once daily, with minimal adverse effects. PROPECIA® has been approved for the treatment of AGA. A comparison of the effect of a formulation described herein and that of PROPECIA® is provided in Example 11 based on the information available on the US Food and Drug Administration website and provided in the PROPECIA® package insert.

The pharmaceutical formulations described herein minimize systemic exposure and thus are safe. The results of the study described in Example 9 of the experimental section demonstrate that cortexolone-17α-propionate solution 5% was well tolerated locally. The incidence of local tolerability signs was low and the incidence of "treatment-emergent" local tolerability signs was generally similar among cortexolone-17α-propionate solution 5% and vehicle treatment groups. Most local tolerability signs were minimal/trace to mild in severity. Scaling and pruritus were most frequently observed "treatment-emergent" signs, with fewer subjects having erythema, folliculitis, and hyperpigmentation. In addition, the incidence of adverse events (AEs) was similar among the two treatment groups, with most events typically mild in severity and not related to the test article. Importantly, no AEs that could be correlated to systemic antiandrogenic activity of cortexolone-17α-propionate (e.g. decrease of libido, erectile dysfunction and ejaculation disorders) occurred during the 6-month treatment. The study of the Example 9 also confirms that the formulations described herein, when topically applied on the scalp, are optimal for achieving a local delivery of the therapeutic agent, meanwhile avoiding its excessive systemic distribution, which may cause the occurrence of antiandrogenic effects in treated subjects. The low levels of circulating cortexolone-17α-propionate, following the application of cortexolone-17α-propionate on the scalp, is also evident from the PK parameters exemplified in Example 6. At least this property differentiates the formulations described herein from finasteride 1 mg tablets (PROPECIA®): as reported in the PROPECIA® package insert, the drug has many side effects, such as decreased libido, erectile dysfunction (impotence), ejaculation disorders, and decreased volume of ejaculate. These adverse events of PROPECIA®, which are reported in 1% of the patients, are caused by the systemic antiandrogenic activity exerted by the therapeutic agent. Differently from PROPECIA®, the formulations described herein are able to maximize the delivery of the therapeutic agent to the target site (i.e. the hair follicle), minimizing its systemic adsorption, which translates into a pharmacological profile characterized by efficacy in promoting hair regrowth (due to local activity on hair follicles), with absence of significant adverse events, including those due to systemic antiandrogenic effects.

It is evident, based on the studies described in the experimental section, that the formulations described herein represent a great improvement with respect to the currently available systemic antiandrogenic drug, PROPECIA®, for the treatment of AGA. An exemplary formulation of the invention, disclosed in Example 4b, when tested in a phase II clinical trial in subjects affected by AGA (with topical applications twice daily on the scalp of the affected area for 6 months), demonstrated to be effective in stimulating the hair growth, as assessed by the two co-primary endpoints (the mean change from baseline in non-vellus TAHC and the subject self-assessment HGA questionnaire), which had a larger magnitude of improvement with respect to the vehicle. As discussed in Example 11, topical administration of this exemplary formulation of Example 4b provided a mean change in non-vellus TAHC at 6 months which was almost identical to that of PROPECIA® at 6 months (12.7 for formulation of Example 4b vs. 12.2 calculated from the published results of two phase III clinical studies for Propecia®), without systemic antiandrogenic effects that are known to be responsible of the main side effects of PROPECIA®, such as decreased libido, erectile dysfunction (impotence) and ejaculation disorders.

The articles "a," "an," and "the" are used herein to refer to one or to more than one (i.e., to at least one) of the grammatical object of the article. By way of example, "an element" means one element or more than one element.

As used herein, the term "about" means ±10% of the specified value, unless otherwise indicated.

As used herein, the phrases "active agent" and "therapeutic agent" are interchangeable and refer to cortexolone-17α-propionate.

The term "alopecia" as used herein refers to, collectively, or individually as specified, androgenetic alopecia (AGA), alopecia areata (including diffuse alopecia areata, alopecia areata monolocularis, alopecia areata multilocularis, ophiasis, alopecia totalis, and alopecia universalis), telogen effluvium, anagen effluvium, and traction alopecia.

As used herein, the term "anhydrous" means substantially free of water, i.e. having less than about 5 weight percent water, and, in certain embodiments as specified herein, less than about 3 weight percent water.

As used herein, the term "antioxidant" includes those pharmaceutically acceptable antioxidants known to those of ordinary skill in the art. Examples include, but are not limited to, butylated hydroxytoluene (BHT), butylated hydroxyanisole (BHA), ascorbyl palmitate, ascorbic acid, alpha tocopherol (also known as Vitamin E), propyl gallate, and the like.

As used herein, the phrase "area under the curve" or "AUC" refers to the area under the curve defined by changes in the plasma concentration of the active agent (or one of its metabolites, as specified) over time following the application of a dose of the active agent itself or a formulation comprising the same. "$AUC_{0-\infty}$" is the area under the concentration-time curve extrapolated from $t_0$ to infinity following the application of a dose. "$AUC_{0-t}$" is the area under the concentration-time curve from time zero to time t following the application of a dose, wherein t is the last time point with a measurable concentration. $AUC_\tau$ refers to mean steady-state AUC.

As used herein, the phrase "$C_1$-$C_7$ alcohol" refers to an alcohol having up to 7 carbons that is suitable for use in a topical pharmaceutical formulation. Examples of such $C_1$-$C_7$ alcohols include, but are not limited to, methanol, ethanol, isopropanol, n-butanol, n-propanol, benzyl alcohol, and the like. Without wishing to be bound by any particular theory, it is believed that $C_1$-$C_7$ alcohols, and particularly short chain $C_1$-$C_7$ alcohols, like ethyl, propyl or isopropyl alcohols, exert a solubilizing activity on cortexolone-17α-propionate. It is further believed that such $C_1$-$C_7$ alcohols contribute to the spreadability of the formulations described herein.

As used herein, the term "$C_{max}$" refers to the maximum concentration of an active agent, or a metabolite thereof, on a graph of the plasma concentration of the active agent (or its metabolite) vs. time. $C_{maxτ}$ refers to the maximum concentration of an active agent, or a degradation product thereof, on a graph of the plasma concentration of the active agent (or its degradation product or metabolite) vs. time when the steady state level has been reached.

As used herein "cortexolone" (also known as "11-Deoxycortisol" or "Reichstein's substance") refers to the compound having the structure:

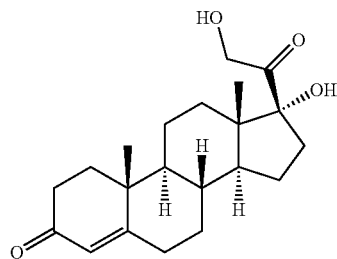

As used herein "cortexolone-17α-propionate" refers to the compound 17α-propionyloxy-21-hydroxy-pregna-4-ene-3,20-dione, which is equivalent to the chemical structure:

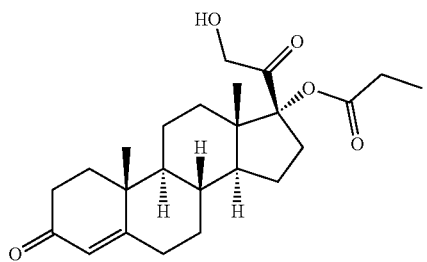

As used herein, the term "metabolite" refers to those compounds that result from the in vivo metabolism or degradation of cortexolone-17α-propionate. Exemplary known metabolites include, but are not limited to, cortexolone and tetrahydrocortexolone.

As used herein, the term "degradation product" refers to those compounds that result from the in vitro degradation of cortexolone-17α-propionate. Exemplary known cortexolone-17α-propionate degradation products include, but are not limited to, cortexolone-21-propionate and cortexolone.

As used herein the term "ester" refers to esterified organic solvents including, but not limited to, ethyl acetate and ethyl lactate.

As used herein the phrase "natural oil" refers to those oils isolable from natural sources. Exemplary natural oils include, but are not limited to, almond oil, olive oil, cottonseed oil, safflower oil, and the like As used herein, the term "polyol" refers to organic molecules containing two or more hydroxyl groups. Exemplary polyols include, but are not limited to, ethylene glycol, propylene glycol, glycerol, hexanetriol, and the like.

As used herein, the phrase "polyol ether" refers to a polyol ether suitable for use in a topical pharmaceutical formulation. Exemplary polyol ethers include, but are not limited to, polypropylene glycol, polyethylene glycol, polyethylene-polypropylene triblock copolymers, dipropylene glycol, diethylene glycol monoethyl ether, and the like.

As used herein, the phrase "penetration enhancer," refers to those pharmaceutically acceptable compounds that increase penetration of the active agent. Exemplary penetration enhancers include, but are not limited to, polyoxyethylene alkyl ethers, polyoxyl glycerides, dimethyl sulfoxide, pyrrolidone, N-methyl-2-pyrrolidone, diethylene glycol monoethyl ether (TRANSCUTOL®), dimethyl isosorbide, diethyl sebacate, azone, menthol, nerol, camphor, methyl salicylate, Tween 80, SDS, benzalkonium chloride, polyoxyl 40 hydrogenated castor oil (CREMOPHOR® RH40, KOLLIPHOR® RH40), didecyldimethylammonium bromide (DDAB), didecyltrimethylammonium bromide (DTAB), fatty acids esters such as isopropyl myristate, isopropyl palmitate and the like, fatty acids such as oleic acid, palmitic acid, linoleic acid, and salts thereof, fatty alcohols such as oleyl alcohol, myristyl alcohol, stearyl alcohol and the like, medium-chain triglycerides, and combinations of any of the foregoing.

As used herein, the term "solvent" means one or a mixture of more than one pharmaceutically acceptable solvents suitable for topical application, including without limitation, the scalp, that is used to solubilize cortexolone-17α-propionate in a formulation described herein.

As used herein "tetrahydrocortexolone" refers to the compound having the Chemical Abstract Service (CAS) Registry Number 68-60-0.

As used herein, the term "$T_{max}$" refers to the time at which maximum plasma concentration of an active agent (or metabolite thereof) is reached after application of the active agent. The term $T_{max}$ refers to the time when the maximum concentration of an active agent, or metabolite thereof, on a graph of the plasma concentration of the active agent (or its metabolite) vs. time when the steady state level has been reached The terms "treat," "treating," and "treatment" refer to any indicia of success in the treatment or amelioration of an injury, disease, or condition, including any objective or subjective parameter such as abatement; remission; diminishing of symptoms or making the injury, disease, or condition more tolerable to the patient; slowing in the rate of degeneration or decline; or improving a patient's physical or mental well-being. The treatment or amelioration of symptoms can be based on objective or subject parameters, including the results of a physical examination, neuropsychiatric examinations, or psychiatric evaluation.

The term "preventing" refers to keeping from happening, existing, or alternatively delaying the onset or recurrence of a disease, disorder, or condition to which such term applies, or of one or more symptoms associated with a disease, disorder, or condition. The term "preventing" also refers to reducing the incidence of a disease, disorder or condition. The term "prevention" refers to the act of preventing.

As used herein, the phrase "weight percent" is intended to encompass and disclose embodiments wherein the weight percent is weight percent by volume (w/v) and percentage of weight by total weight (w/w) for a given value. By way of example, an embodiment comprising 10 weight percent of element "X" discloses embodiments comprising both 10 weight percent "X" (w/v) and 10 weight percent "X" (w/w).

Similarly, and again by way of example, an embodiment comprising 10 weight percent "X," 20 weight percent "Y," and 60 weight percent "Z," discloses embodiments comprising: a) 10 weight percent "X" (w/v), 20 weight percent "Y" (w/v), and 60 weight percent "Z" (w/v); and b) 10 weight percent "X" (w/w), 20 weight percent "Y" (w/w), and 60 weight percent "Z" (w/w). The foregoing notwithstanding, in certain embodiments, a value will be marked specifically "(w/w)" or "(w/v)." In those instances, the value should be interpreted as disclosing only the labeled value, i.e. only (w/w) or only (w/v)—but not both.

As used herein, the terms "comprises," "comprising," "having," "including," "containing," and the like are open-ended terms meaning "including, but not limited to." To the extent a given embodiment disclosed herein "comprises" certain elements, it should be understood that present disclosure also specifically contemplates and discloses embodiments that "consist essentially of" those elements and that "consist of" those elements.

As used herein the terms "consists essentially of," "consisting essentially of," and the like are to be construed as a semi-closed terms, meaning that no other ingredients which materially affect the basic and novel characteristics of an embodiment are included.

As used herein, the terms "consists of," "consisting of," and the like are to be construed as closed terms, such that an embodiment "consisting of" a particular set of elements excludes any element, step, or ingredient not specified in the embodiment.

As used herein, the terms "Target Area Hair Count" or "TAHC" refer to the change, from baseline, in the number of non-vellus hairs in a target area of the scalp. The target area can be, for example, 1 cm$^2$ or a circle of a diameter of 1 inch (5.1 cm$^2$).

As used herein, the terms "Hair Growth Assessment" or "HGA" refer to a score given by the subject comparing the baseline standardized global photo of the subject's scalp with a "real time" standardized global photo.

As used herein, the terms "Investigator's Global Assessment" or "IGA" refer to a score given by an evaluator comparing the baseline standardized global photo of the subject's scalp with a "real time" standardized global photo.

As used herein, the term "Bis In Die" or "BID" means "twice a day".

As used herein, the term "allocation group" refers to a group of people participating in a clinical trial that are randomly allocated to either the group receiving the treatment under investigation or to a group receiving standard treatment (or placebo treatment) as the control.

As used herein, the term "ethanol," means ethyl alcohol, i.e. $CH_3CH_2OH$, and includes pure (absolute) ethanol and 96° ethanol, the latter being ethanol containing water in an amount typically ranging from about 4% to about 5.1% by volume.

The present disclosure provides fully solubilized pharmaceutical formulations of cortexolone-17α-propionate comprising a solvent and at least 2.1 weight percent cortexolone-17α-propionate up to about 20 weight percent cortexolone-17α-propionate, including all intermediate values there between. In particular embodiments, the formulation can comprise at least 2.1 weight percent up to about 17 weight percent cortexolone-17α-propionate, at least 2.5 weight percent up to about 17 weight percent cortexolone-17α-propionate, at least 2.5 weight percent up to about 15 weight percent cortexolone-17α-propionate, or at least 3 weight percent up to about 15 weight percent cortexolone-17α-propionate. In other embodiments, the formulation can comprise about 6, about 7, about 7.5, about 8, about 9, about 10, about 11, about 12, about 13, about 14, or about 15 weight percent of cortexolone-17α-propionate.

The present disclosure also provides fully solubilized pharmaceutical formulations of cortexolone-17α-propionate comprising a solvent and at least 2.1 weight percent cortexolone-17α-propionate up to about 5.5 weight percent cortexolone-17α-propionate, including all intermediate values there between. In particular embodiments, the formulation can comprise at least 2.2 up to about 5.5 weight percent cortexolone-17α-propionate, at least 2.3 up to about 5.5 weight percent cortexolone-17α-propionate, at least 2.4 up to about 5.5 weight percent cortexolone-17α-propionate, at least 2.5 up to about 5.5 weight percent cortexolone-17α-propionate, at least 2.6 up to about 5.5 weight percent cortexolone-17α-propionate, at least 2.7 up to about 5.5 weight percent cortexolone-17α-propionate, at least 2.8 up to about 5.5 weight percent cortexolone-17α-propionate, at least 2.9 up to about 5.5 weight percent cortexolone-17α-propionate, or at least 3.0 up to about 5.5 weight percent cortexolone-17α-propionate. In other embodiments, the formulation can comprise about 2.3, about 2.5, about 3, about 3.5, about 4, about 4.5, about 5, or about 5.5 weight percent cortexolone-17α-propionate. In a particular embodiment, the formulation can comprise about 5 weight percent of cortexolone-17α-propionate. In each of these embodiments, the cortexolone-17α-propionate is fully solubilized in the formulation. As used herein, "fully solubilized" means at least 95 weight percent, at least 98 weight percent, at least 99 weight percent, or at least 99.9 weight percent of the cortexolone-17α-propionate is solubilized in the formulation.

Cortexolone-17α-propionate solubility exceeding 2 weight percent has not been previously reported and was difficult to achieve. For Example, WO 2009/019138 discloses formulations having up to 2 weight percent cortexolone-17α-propionate, but does not teach or suggest whether higher concentration formulations can be prepared or how such formulation should be prepared.

Similarly, Celasco, et al., Arzneim.-Forsch./Drug Res. 54, No. 12, 881-886 (2004), teaches suspending a 5 mg sample of cortexolone-17α-propionate in 0.2 ml suspending vehicle. But like WO 2009/019138, Celasco is silent on whether fully solubilized high-concentration formulations can or should be prepared.

In certain embodiments, the formulation is anhydrous and includes less than about 5 weight percent water. In further embodiments, the anhydrous formulation includes less than about 3 weight percent water.

In certain embodiments, the formulation can be a liquid (including, for example, a solution or a suspension or an emulsion or a microemulsion) or can be semi-solid (including, for example, a cream, a gel, or an ointment, or a foam). Regardless of the form of the formulation (solution, gel, emulsion, etc.), the formulation has a suitable consistency to be spread on the scalp and/or on the skin.

In one embodiment, the formulation can be a liquid formulation.

In another embodiment, the formulation can be anhydrous. In another embodiment, the formulation can be a solution. In some embodiments, the solution is anhydrous having less than about 5 weight percent water. In other embodiments, the anhydrous solution has less than about 3 weight percent water.

In one embodiment, the present disclosure provides a pharmaceutical formulation suitable for topical administration wherein the formulation comprises cortexolone-17α- propionate in an amount of at least 2.1 weight percent and one or more pharmaceutically acceptable solvents.

In another embodiment, the present disclosure provides a pharmaceutical formulation suitable for topical administration wherein the formulation comprises cortexolone-17α-propionate in an amount ranging from about 2.1 weight percent to about 20 weight percent and one or more pharmaceutically acceptable solvents. Suitable ranges and amounts of cortexolone-17α-propionate in this aspect of the invention are described above in connection with topical pharmaceutical formulations comprising cortexolone-17α-propionate.

In another embodiment, the present disclosure provides a pharmaceutical formulation suitable for topical administration wherein the formulation comprises cortexolone-17α-propionate in an amount ranging from about 2.1 weight percent to about 5.5 weight percent and one or more pharmaceutically acceptable solvents. Suitable ranges and amounts of cortexolone-17α-propionate in this aspect of the invention are described above in connection with topical pharmaceutical formulations comprising cortexolone-17α-propionate.

In still another embodiment, the present disclosure provides a pharmaceutical formulation suitable for topical administration for use in the treatment and/or prevention of alopecia, wherein the formulation comprises cortexolone-17α-propionate in an amount of at least 2.1 weight percent and one or more pharmaceutically acceptable solvents.

In another embodiment, the present disclosure provides a pharmaceutical formulation suitable for topical administration for use in the treatment and/or prevention of alopecia, wherein the formulation comprises cortexolone-17α-propionate in an amount ranging from about 2.1 weight percent to about 20 weight percent and one or more pharmaceutically acceptable solvents. Suitable ranges and amounts of cortexolone-17α-propionate in this aspect of the invention are described above in connection with topical pharmaceutical formulations comprising cortexolone-17α-propionate.

In yet another embodiment, the present disclosure provides a pharmaceutical formulation suitable for topical administration for use in the treatment and/or prevention of alopecia, wherein the formulation comprises cortexolone-17α-propionate in an amount ranging from about 2.1 weight percent to about 5.5 weight percent and one or more pharmaceutically acceptable solvents. Suitable ranges and amounts of cortexolone-17α-propionate in this aspect of the invention are described above in connection with topical pharmaceutical formulations comprising cortexolone-17α-propionate.

In another embodiment, the present disclosure provides a method for treating and/or preventing alopecia in a mammal in need thereof, the method comprising topically administering a effective amount of a pharmaceutical formulation suitable for topical administration, wherein the formulation comprises cortexolone-17α-propionate in an amount of at least 2.1 weight percent and one or more pharmaceutically acceptable solvents.

A further aspect of the invention is a method for treating and/or preventing alopecia in a mammal in need thereof, said method comprising the topical administration of a therapeutic amount of a pharmaceutical formulation suitable for topical administration, wherein the formulation comprises cortexolone-17α-propionate in an amount ranging from about 2.1 weight percent to about 20 weight percent and one or more pharmaceutically acceptable solvents. Suitable ranges and amounts of cortexolone-17α-propionate in this aspect of the invention are described above in connection with topical pharmaceutical formulations comprising cortexolone-17α-propionate.

A further aspect of the present invention is a method for treating and/or preventing alopecia in a mammal in need thereof, said method comprising the topical administration of a therapeutic amount of a pharmaceutical formulation suitable for topical administration, wherein said formulation comprises cortexolone-17α-propionate in an amount ranging from about 2.1 weight percent to about 5.5 weight percent and one or more physiologically acceptable solvents. Suitable ranges and amounts of cortexolone-17α-propionate in this aspect of the invention are described above in connection with topical pharmaceutical formulations comprising cortexolone-17α-propionate.

In certain embodiments, the mammal is a human.

In particular embodiments, topical administration comprises application of the formulation to the skin and/or the scalp.

In particular embodiments, the alopecia is androgenetic alopecia (AGA), alopecia areata (including diffuse alopecia areata, alopecia areata monolocularis, alopecia areata multilocularis, ophiasis, alopecia totalis and alopecia universalis), telogen effluvium, anagen effluvium, and traction alopecia. In particular embodiments, the alopecia is AGA.

In certain embodiments, the pharmaceutical formulation can be in form of a solution, a gel, a fluid ointment, a suspension, a microemulsion, or a foam.

In addition to the solvent and the specified amount of cortexolone-17α-propionate, the formulation described herein can also optionally contain at least one penetration enhancer, and optionally at least one pharmaceutically acceptable excipient.

In certain embodiments, the formulation can further include at least one antioxidant, at least one emulsifier, or a combination of the foregoing.

The Solvent

In certain embodiments, the solvent can be anhydrous including less than about 5 weight percent water. In other embodiments, the solvent can be anhydrous and include less than about 3 weight percent water.

In certain embodiments, the solvent can be selected from the group comprising or the group consisting of: water, a $C_1$-$C_7$ alcohol, a polyol ether, a polyol, a natural oil, an ester, tricaprylin (2,3-di(octanoyloxy)propyl octanoate), a medium-chain triglyceride, caprylocaproyl polyoxyl-8 glycerides, and combinations of any of the foregoing.

In some embodiments, the formulation can comprise at least about 50 weight percent solvent. In other embodiments, the formulation can comprise at least about 60 weight percent solvent. In other embodiments, the formulation can comprise at least about 70 weight percent solvent. In other embodiments, the formulation can comprise at least about 80 weight percent solvent. In other embodiments, the formulation can comprise at least about 85 weight percent solvent, at least about 90 weight percent solvent, at least about 91 weight percent solvent, at least about 92 weight percent solvent; at least about 93 weight percent solvent; at least about 94 weight percent solvent; or at least about 95 weight percent solvent.

In certain embodiments, the solvent can comprise a mixture of a $C_1$-$C_7$ alcohol, a polyol ether, a polyol. In such embodiments, the formulation can comprise from about 10 to about 50 weight percent of the polyol ether; from about 5 weight percent to about 55 weight percent of the polyol;

and about 5 to about 50 weight percent of the $C_1$-$C_7$ alcohol. In a particular embodiment, the mixture of the $C_1$-$C_7$ alcohol, the polyol ether, and the polyol can be present at about a 1:1:1 ratio on a w/w/w basis. In certain embodiments, each of the $C_1$-$C_7$ alcohol, the polyol ether, and the polyol are present at about 30 weight percent.

In particular embodiments, the formulation can comprise from about 15 to about 45 weight percent of the polyol ether; from about 20 to about 40 weight percent of the polyol ether; from about 25 to about 35 weight percent of the polyol ether; or from about 30 to about 35 weight percent of the polyol ether. In particular embodiments, the formulation can comprise about 30 weight percent of the polyol ether. In other embodiments, the formulation can comprise about 32 weight percent of the polyol ether.

In particular embodiments, the polyol ether is selected from the group comprising or the group consisting of: polyethylene glycol, polypropylene glycol, polyethylene-polypropylene triblock copolymers, dipropylene glycol, diethylene glycol monoethyl ether (TRANSCUTOL®), and combinations thereof.

When the polyol ether is a polyethylene glycol, it can be selected from the group comprising or the group consisting of: polyethylene glycol 200, polyethylene glycol 300, polyethylene glycol 400, polyethylene glycol 540, and polyethylene glycol 600. In particular embodiments, the polyol ether can be polyethylene glycol 200. In other embodiments, the polyol ether can be polyethylene glycol 400. In still other embodiments, the polyol ether can be diethylene glycol monoethyl ether.

In particular embodiments, the polyol can be selected from the group comprising or the group consisting of: propylene glycol, ethylene glycol, glycerol, hexanetriol, and combinations thereof. In particular embodiments, the polyol can be glycerol. In other embodiments, the polyol can be propylene glycol.

In particular embodiments, the polyol can be present in an amount ranging from about 5 weight percent to about 55 weight percent of the total formulation; from about 10 weight percent to about 50 weight percent of the total formulation; from about 20 weight percent to about 45 weight percent of the total formulation; and in certain embodiments, from about 25 weight percent to about 40 weight percent. In a particular embodiment, the polyol comprises about 30 weight percent of the total formulation. In a further embodiment, the polyol comprising about 30 weight percent of the total formulation can be propylene glycol.

In some embodiments, the formulation can comprise from about 5 to about 50 weight percent of the $C_1$-$C_7$ alcohol. In particular embodiments, the formulation can comprise from about 15 to about 45 weight percent of the $C_1$-$C_7$ alcohol; from about 20 to about 40 weight percent of the $C_1$-$C_7$ alcohol; or from about 25 to about 35 weight percent of the $C_1$-$C_7$ alcohol. In particular embodiments, the formulation can comprise about 30 weight percent of the $C_1$-$C_7$ alcohol. In still further embodiments, the formulation can comprise the $C_1$-$C_7$ alcohol in an amount ranging from about 10 weight percent to about 40 weight percent, or from about 15 weight percent to about 35 weight percent.

In particular embodiments, the $C_1$-$C_7$ alcohol is selected from the group comprising or the group consisting of: methanol, ethanol, isopropanol, n-butanol, n-propanol, and benzyl alcohol. In particular embodiments, the $C_1$-$C_7$ alcohol is ethanol. In some embodiments, the ethanol comprises about 30 weight percent of the total formulation. In other embodiments, the $C_1$-$C_7$ alcohol is isopropanol.

In some embodiments, the $C_1$-$C_7$ alcohol can contain a small water fraction, generally in the range of from about 4 percent to about 5.1 percent by volume. In embodiments wherein the formulation is anhydrous, the $C_1$-$C_7$ alcohol having from about 4 percent to about 5.1 percent water by volume can be present in the formulation in an amount such that the water content in the finished formulation itself is less than about 5 weight percent or less than about 3 weight percent.

In certain embodiments, the solvent can comprise a polyol, a polyol ether, and a Cr $C_7$ alcohol. In particular embodiments, the solvent can comprise ethanol as the $C_1$-$C_7$ alcohol, diethylene glycol monomethyl ether as the polyol ether, and propylene glycol as the polyol. These solvents can be present in any acceptable ratio, but typically are present such that each is about 25 to about 35 weight percent of the formulation.

Penetration Enhancers

In certain embodiments, in addition to the solvent, the formulations disclosed herein can include one or more penetration enhancers. Without wishing to be bound by a particular theory, penetration enhancers are believed to beneficially affect delivery of the therapeutic agent into the skin (including the scalp) and/or the hair follicles. Advantageously, and in some embodiments, the solvent or some component(s) of the solvent act as a penetration enhancer. For example, in embodiments wherein the formulation comprises ethanol and/or diethylene glycol monoethyl ether, these solvents can also act to enhance penetration of the active agent into the skin (including the scalp) and/or the follicles. The presence of ethanol and/or diethylene glycol monoethyl ether notwithstanding, the formulations described herein can optionally further include additional penetration enhancers.

Examples of further penetration enhancer that can be incorporated into formulations described herein include, but are not limited to, polyoxyethylene alkyl ethers, polyoxyl glycerides, dimethyl sulfoxide, pyrrolidone, N-methyl-2-pyrrolidone, diethylene glycol monoethyl ether (TRANSCUTOL®), dimethyl isosorbide, diethyl sebacate, azone, menthol, nerol, camphor, methyl salicylate, Tween 80, SDS, benzalkonium chloride, polyoxyl 40 hydrogenated castor oil (CREMOPHOR® RH40, KOLLIPHOR® RH40), didecyldimethylammonium bromide (DDAB), didecyltrimethylammonium bromide (DTAB), fatty acids esters such as isopropyl myristate, isopropyl palmitate and the like, fatty acids such as oleic acid, palmitic acid, linoleic acid, and salts thereof, fatty alcohols such as oleyl alcohol, myristyl alcohol, stearyl alcohol and the like, medium-chain triglycerides, and combinations of any of the foregoing.

In one embodiment, the penetration enhancer is dimethyl isosorbide. In another embodiment, the penetration enhancer is a mixture comprising dimethyl isosorbide and diethylene glycol monoethyl ether. In another embodiment, the at least one penetration enhancer is dimethyl sulfoxide.

In certain embodiments, the penetration enhancer can be present in an amount ranging from about 1 weight percent to about 50 weight percent with respect to the total weight of the formulation. In other embodiments, the penetration enhancer can be present from about 2 weight percent to about 40 weight percent with respect to the total weight of the formulation; or from about 5 weight percent to about 35 weight percent with respect to the total weight of the formulation. According to some embodiments, the skin penetration enhancer can be present in the formulation described herein in an amount of about 1% weight percent, about 2 weight percent, about 5 weight percent, about 10 weight percent, about 15 weight percent, about 20 weight percent, about 25 weight percent, about 30 weight percent, about 35 weight percent, about 40 weight percent, about 45 weight percent, or about 50 weight percent with respect to the total weight of the formulation.

Other Ingredients

Because oxidation can result in degradation of the active agent, in some embodiments, the formulation can further include up to about 1 weight percent of an antioxidant. The antioxidant can be selected from the group comprising or the group consisting of: BHT, BHA, ascorbyl palmitate, ascorbic acid, alpha tocopherol (also known as Vitamin E), propyl gallate, and combinations of any of the foregoing.

In particular embodiments, the formulation can include up to about 0.5 weight percent of an antioxidant or include about 0.5 weight percent antioxidant. In particular embodiments, the antioxidant can be ascorbyl palmitate. In other embodiments, the antioxidant can be BHA. In still other embodiments, the antioxidant can be BHT. In still further embodiments, formulation can include about 0.5 weight percent ascorbyl palmitate.

In some embodiments, the formulation can further include an emulsifier. Without wishing to be bound to any particular theory, it is believed that emulsifiers, when present, assist or facilitate dissolution of any solid substances, such as the active agent, in the formulation. In other embodiments, however, the emulsifier can be present to facilitate incorporation of two non-miscible liquids into each other (e.g. an emulsion or microemulsion).

In other embodiments, and without wishing to be bound by any particular theory, an emulsifier can increase product spreadability. For example, and without wishing to be bound to a particular theory, when the formulation is a liquid solution, the presence of a suitable amount of an emulsifier is believed to decrease the surface tension between the formulation and the lipid environment of the superficial layer of the skin and/or scalp. This makes it easier to spread the formulation and is believed to assist penetration of the therapeutic agent into skin (including the scalp) and/or hair follicles.

In certain embodiments, the emulsifier can be selected from the group comprising or the group consisting of: polyethylene glycol (PEG)-fatty acid monoesters such as PEG-15 hydroxystearate (also known as polyoxyl-15-hydroxystearate), PEG-30 stearate, PEG-40 laurate, PEG-40 oleate and the like; polyoxyethylene sorbitan fatty acid esters such as polysorbate 20, polysorbate 60, polysorbate 80 and the like; polyoxyethylene alkyl ethers such as PEG-20 cetostearyl ether, polyoxyl 25 cetostearyl, cetomacrogol 1000 and the like; sorbitan fatty acid esters such as sorbitan monolaurate, sorbitan monopalmitate, sorbitan monooleate, and the like; propylene glycol esters of fatty acids; polyglycerol esters of fatty acids; polyoxyethylene castor oil derivatives such as polyoxyl 5 castor oil, polyoxyl 15 castor oil, polyoxyl 35 castor oil, polyoxyl 40 hydrogenated castor oil and the like; caprylocapryl polyoxyil-glycerides; polyoxylglycerides such as caprylocaproyl polyoxylglycerides, lauroyl polyoxylglycerides, oleoyl polyoxylglycerides, and the like; along with combinations of any of the foregoing.

In particular embodiments, the formulation can include the emulsifier in an amount of up to about 0.5 weight percent of the total formulation. In some embodiments, the emulsifier can be present in an amount ranging from 0.05 to 0.2 weight percent. In still further embodiments, the formulation can include the emulsifier in an amount up to about 0.1 weight percent or it can include about 0.1 weight percent emulsifier. In particular embodiments, the emulsifier can be polyoxyl 40 hydrogenated castor oil. In other embodiments, the emulsifier can be polyoxyl-15-hydroxystearate. In particular embodiments, the emulsifier can be polysorbate 80. In still further embodiments, the emulsifier is present in the formulation at about 0.1 weight percent.

Pharmacokinetic Parameters

It has been surprisingly found that the formulations described herein provide acceptable pharmacokinetics profiles of both cortexolone-17α-propionate and/or its metabolites and that the formulations described herein appear to provide excellent local delivery of the therapeutic agent while minimizing systemic exposure. This is a beneficial result because, without wishing to be bound by any particular theory, it is believed that the active agent is most effective when delivered to the hair follicles directly, rather than through the systemic circulation. Thus, it is an advantage of formulations of the present disclosure to be able to deliver the active agent with sufficient penetration to reach the follicles, but without so much penetration as to be widely systemically available after topical application.

For example, in certain embodiments, the formulations described herein provide a mean steady-state $C_{max}$ of cortexolone-17α-propionate of about 2 ng/ml to about 6 ng/ml; of about 2.5 ng/ml to about 5.5 ng/ml; or of about 3 ng/ml to about 5 ng/ml. In certain embodiments the mean steady-state $C_{max}$ of cortexolone-17α-propionate can be about 4 ng/ml, or about 3.8 ng/ml. In other embodiments, the mean steady-state $C_{max}$ can be less than about 6 ng/ml, less than about 5 ng/ml, less than about 4 ng/ml, less than about 3 ng/ml, or less than about 2 ng/ml.

In certain embodiments, the formulation described herein provides a mean steady-state $T_{max}$ of cortexolone-17α-propionate of from about 2 to about 7 hours; from about 2.5 to about 6.5 hours; from about 3 to about 6 hours; from about 3.5 to about 5 hours; or from about 4 to about 5 hours. In particular embodiments, the mean steady-state $T_{max}$ of cortexolone-17α-propionate can be about 4.5 or 4.4 hours. In certain embodiments, the mean steady-state $T_{max}$ of cortexolone-17α-propionate can be less than about 8 hours, less than about 7 hours, less than about 6 hours, less than about 5 hours, or less than about 4 hours.

The present formulation also provides a desirable $AUC_T$ of from about 20 (ng*h)/ml to about 55 (ng*h)/ml; of from about 25 (ng*h)/ml to about 50 (ng*h)/ml; of from about 25 (ng*h)/ml to about 45 (ng*h)/ml; or from about 30 (ng*h)/ml to about 40 (ng*h)/ml. In certain embodiments, the mean $AUC_T$ can be about 35 (ng*h)/ml or about 37 (ng*h)/ml. In other embodiments, the $AUC_T$ can be less than about 55 (ng*h)/ml, less than about 45 (ng*h)/ml, less than about 40 (ng*h)/ml, or less than about 35 (ng*h)/ml.

The present formulation also provides a desirable excretion profile for cortexolone-17α-propionate. For example, after initial topical application of the formulation, in certain embodiments, less than about 0.5 percent of the cortexolone-17α-propionate administered can be detected in a patient's urine. In other embodiments, less than about 0.4, less than about 0.35, less than about 0.3, or less than about 0.25, less than about 0.2, or less than about 0.15 percent of the cortexolone-17α-propionate can be detected in a given patient's urine. In certain embodiments, no cortexolone-17α-propionate is detectable in a given patient's urine.

In certain embodiments, after steady state has been achieved, less than about 700 µg of the cortexolone-17α-propionate administered can be detected in a patient's urine. In other embodiments, less than about 650, less than about 600, less than about 500, less than about 400, less than about 300, or less than about 250 µg of the cortexolone-17α-propionate can be detected in a given patient's urine. In certain embodiments, even after steady state has been achieved, no cortexolone-17α-propionate can be detected in a given patient's urine.

In certain embodiments, cortexolone can also be detected in a patient's urine. For example, in certain embodiments after initial topical application of the formulation less than about 0.5 µg of cortexolone can be detected in a patient's urine. In other embodiments, less than about 0.4, less than about 0.35, less than about 0.3, or less than about 0.25, less than about 0.2, or less than about 0.15 µg of cortexolone can be detected in a given patient's urine. In certain embodiments, no cortexolone can be detected in a given patient's urine.

After steady state has been achieved, and in certain embodiments, less than about 2 µg of cortexolone can be detected in a patient's urine. In other embodiments, less than about 1.75, less than about 1.5, less than about 1.25, less than about 1, less than about 0.75, or less than about 0.5 µg of the cortexolone can be detected in a given patient's urine. In certain embodiments, even after steady state has been achieved, no cortexolone can be detected in a given patient's urine.

In certain embodiments, tetrahydrocortexolone can also be detected in a patient's urine. For example, in certain embodiments after initial topical application of the formulation less than about 150 µg of tetrahydrocortexolone can be detected in a patient's urine. In other embodiments, less than about 125, less than about 100, less than about 75, less than about 65, less than about 55, or less than about 50 µg of tetrahydrocortexolone can be detected in a given patient's urine. In certain embodiments, no tetrahydrocortexolone can be detected in a given patient's urine.

After steady state has been achieved, and in certain embodiments, less than about 400 µg of tetrahydrocortexolone can be detected in a patient's urine. In other embodiments, less than about 350, less than about 325, less than about 300, less than about 225, less than about 150, or less than about 230 µg of the tetrahydrocortexolone can be detected in a given patient's urine. In certain embodiments, even after steady state has been achieved, no tetrahydrocortexolone can be detected in a given patient's urine.

Modes of Administration

The formulations described herein can be administered according to varying schedules. In one embodiment, the mode of administration of the formulations can be continuous. For example, the formulations can be applied topically once a day, twice daily, three times a day, four times a day, or more, as specified by a physician. In particular embodiments, a formulation described herein can be applied topically once a day or twice daily. According to a particular embodiment, the formulation described herein can be applied topically once a day. According to another embodiment, the formulation described herein can be applied topically twice daily.

In certain embodiments, a dosing regimen can be tapered. That is, the formulation can be applied once a day for a first period of time, twice daily thereafter for a second period of time, three times a day thereafter for a third period of time, and so on. In a particular embodiment, the formulation can be applied once a day on the first day, and twice daily thereafter, with the appropriate duration of treatment determined by a subject's physician.

In certain embodiments, the formulation can be applied over the course of a period of days, weeks, or months. For example, the formulation can be applied one, two, three, four, or five times a day for up to: 1, 2, 3, 4, 5, 6, or 7 days; about 2 weeks, about 3 weeks, or about 4 weeks; about 2 months, about 3 months, about 4 months, about 5 months, about 6 months, about 7 months, about 8 months, about 9 months, about 10 months, about 11 months, about a year (i.e. about 12 months), about 13 months, about 14 months, about 15 months, about 16 months, about 17 months, about 18 months, about 19 months, about 20 months, about 21 months, about 22 months, about 23 months or about 24 months. According to a particular embodiment, the formulation can be applied once on the first day and twice daily thereafter for about 4 weeks.

In another embodiments, the formulation can be topically applied to the scalp once a day for 1 month, once a day for 2 months, once a day for 3 months, once a day for 4 months, once a day 5 months, once a day for 6 months, once a day for 8 months, once a day for 12 months, once a day for 14 months, once a day for 16 months, once a day for 18 months, once a day for 20 months, once a day for 22 months, or once a day for 24 months. In certain embodiments, the formulation can be topically applied on the scalp once daily for 6 months. In certain embodiments, the formulation can be topically applied on the scalp once daily for 12 months.

In other embodiments, the formulation can be topically applied on the scalp twice daily for about 1 month, for about 2 months; for about 3 months; for about 4 months; for about 5 months; for about 6 months, for about 8 months, for about 12 months, for about 14 months, for about 16 months, for about 18 months, for about 20 months, for about 22 months, or for about 24 months. In certain embodiments, the formulation can be topically applied on the scalp twice daily for 6 months. In certain embodiments, the formulation can be topically applied on the scalp twice daily for 12 months.

In other embodiments, the formulation can be applied more than twice daily (i.e. TID, QID, etc) for about 1 month, for about 2 months; for about 3 months; for about 4 months; for about 5 months; for about 6 months, for about 8 months, for about 12 months, for about 14 months, for about 16 months, for about 18 months, for about 20 months, for about 22 months, or for about 24 months. In certain embodiments, the formulation can be topically applied on the scalp more than twice daily (i.e. TID, QID, etc) for 6 months. In certain embodiments, the formulation can be topically applied on the scalp more than twice daily (i.e. TID, QID, etc) for 12 months.

In another embodiment, the mode of administration of the formulations can be cyclic. For example, the formulations can first be applied in a continuous way as described above for a desired period of time, the application is then discontinued for a period of time, such as a few days, and then the application of the formulations is started again as described above. The treatment period can include one or more cycles which can be the same or different. In certain embodiments, the treatment period can be as follows: a) the formulation is topically applied on the scalp for a period of time, such as 4 months, by continuous administration, b) the application is discontinued for a few days, such as 2-5 days, and 3) the topical application is continued for an additional period of time, such as 6 months.

The amount of cortexolone-17α-propionate that can be applied to a patient in need thereof can vary. In some embodiments, about 400 mg of cortexolone-17α-propionate can be applied, about 375 mg of cortexolone-17α-propionate can be applied, about 350 mg of cortexolone-17α-propionate can be applied, about 325 mg of cortexolone-17α-propionate can be applied, about 300 mg of cortexolone-17α-propionate can be applied, about 275 mg of cortexolone-17α-propionate can be applied, about 250 mg of cortexolone-17α-propionate can be applied, or about 225 mg of cortexolone-17α-propionate can be applied. In some embodiments, about 200 mg of cortexolone-17α-propionate can be applied, about 175 mg of cortexolone-17α-propionate can be applied, about 150 mg of cortexolone-17α-propionate can be applied, about 125 mg of cortexolone-17α-propionate can be applied, about 100 mg of cortexolone-17α-propionate can be applied, about 75 mg of cortexolone-17α-propionate can be applied, about 50 mg of cortexolone-17α-propionate can be applied, about 25 mg of cortexolone-17α-propionate can be applied, about 12.5 mg of cortexolone-17α-propionate can be applied, or about 6.25 mg of cortexolone-17α-propionate can be applied. Determination of the appropriate amount of the formulation that should be administered to a given patient in a single application is within the skill of the ordinarily skilled physician.

In particular embodiments, the amount of cortexolone-17α-propionate in a single application can range from about 20 mg to about 400 mg. In other embodiments, the amount of cortexolone-17α-propionate in a single application can range from about 20 mg to about 350 mg. In other embodiments, the amount of cortexolone-17α-propionate in a single application can range from about 20 mg to about 300 mg. In other embodiments, the amount of cortexolone-17α-propionate in a single application can range from about 20 mg to about 250 mg.

In particular embodiments, the amount of cortexolone-17α-propionate in a single application can range from about 20 mg to about 200 mg. In other embodiments, the amount of cortexolone-17α-propionate in a single application can range from about 20 mg to about 170 mg. In other embodiments, the amount of cortexolone-17α-propionate in a single application can range from about 20 mg to about 150 mg. In particular embodiments, the amount of cortexolone-17α-propionate in a single application can range from about 20 mg to about 100 mg. In particular embodiments, the amount of cortexolone-17α-propionate in a single application can be about 20 mg, about 25 mg, about 30 mg, about 35 mg, about 40 mg, about 45 mg, about 50 mg, about 55 mg, about 60 mg, about 75 mg, about 80 mg, about 85 mg, about 90 mg, or about 100 mg. In another embodiment, the amount of cortexolone-17α-propionate in a single application can be about 25 mg. In another embodiment, the amount of cortexolone-17α-propionate in a single application can be about 30 mg. In yet another embodiment, the amount of cortexolone-17α-propionate in a single application can be about 50 mg. In yet another embodiment, the amount of cortexolone-17α-propionate in a single application can be about 75 mg. In yet another embodiment, the amount of cortexolone-17α-propionate in a single application can be about 80 mg. In yet another embodiment, the amount of cortexolone-17α-propionate in a single application can be about 100 mg. In other embodiments, the amount of cortexolone-17α-propionate in a single application can be about 110 mg, about 111 mg, about 112 mg, about 113 mg, about 114 mg, about 115 mg, about 116 mg, about 117 mg, about 118 mg, about 119 mg, or about 200 mg. In yet another embodiment, the amount of cortexolone-17α-propionate in a single application can be about 150 mg.

By way of example only, about 50 mg of cortexolone-17α-propionate could be administered in 1 ml of an embodiment of a formulation disclosed herein, wherein the formulation comprises about 5 weight percent cortexolone-17α-propionate.

In some embodiments, the formulation can be self-administered by the patient once a day or twice daily. In particular embodiments, when the formulation is in liquid form having an active agent concentration of about 5 weight percent, the formulation can be self-administered once a day or twice daily at a dose ranging from about 0.2 to about 2.0 ml, from about 0.5 to about 1.5 ml, and in further embodiments at about 1 ml.

In other embodiments, when the formulation is in liquid form having an active agent concentration of about 2.5 weight percent, the formulation can be self-administered once a day or twice daily at a dose ranging from about 0.2 to about 2.0 ml, from about 0.5 to about 1.5 ml, and in further embodiments at about 1 ml.

In other embodiments, when the formulation is in liquid form having an active agent concentration of about 3 weight percent, the formulation can be self-administered once a day or twice daily at a dose ranging from about 0.2 to about 2.0 ml, from about 0.5 to about 1.5 ml, and in further embodiments at about 1 ml.

In other embodiments, when the formulation is in liquid form having an active agent concentration of about 7.5 weight percent, the formulation can be self-administered once a day or twice daily at a dose ranging from about 0.2 to about 2.0 ml, from about 0.5 to about 1.5 ml, and in further embodiments at about 1 ml.

In other embodiments, when the formulation is in liquid form having an active agent concentration of about 8 weight percent, the formulation can be self-administered once a day or twice daily at a dose ranging from about 0.2 to about 2.0 ml, from about 0.5 to about 1.5 ml, and in further embodiments at about 1 ml.

In other embodiments, when the formulation is in liquid form having an active agent concentration of about 10 weight percent, the formulation can be self-administered once a day or twice daily at a dose ranging from about 0.2 to about 2.0 ml, from about 0.5 to about 1.5 ml, and in further embodiments at about 1 ml.

In other embodiments, when the formulation is in liquid form having an active agent concentration of about 15 weight percent, the formulation can be self-administered once a day or twice daily at a dose ranging from about 0.2 to about 2.0 ml, from about 0.5 to about 1.5 ml, and in further embodiments at about 1 ml.

In other embodiments, when the formulation is in liquid form having an active agent concentration of about 20 weight percent, the formulation can be self-administered once a day or twice daily at a dose ranging from about 0.2 to about 2.0 ml, from about 0.5 to about 1.5 ml, and in further embodiments at about 1 ml.

The formulation described herein can be applied to any body surface in need of treatment, such as the scalp, face (e.g., the eyebrow, eyelashes, upper lip, lower lip, chin, cheeks, beard area, or mustache area), arms, armpits, legs, chest, abdomen, or any combination of the foregoing. In certain embodiments, treatment is not delivered to the face. In other embodiments, the formulation can be applied to the scalp.

Efficacy Parameters

It has been surprisingly found that the pharmaceutical formulations described herein are able to maximize the delivery of the therapeutic agent cortexolone-17α-propionate to the target site (i.e. the hair follicle), minimizing its systemic adsorption. Thus, it is an advantage of the pharmaceutical formulations of the present disclosure to be able to deliver the active agent with sufficient penetration to reach the follicles, but without so much penetration as to be widely systemically available after topical application. This translates into a pharmacological profile characterized by efficacy in promoting hair regrowth (local activity on hair follicles), with absence of significant adverse events, including those due to systemic antiandrogenic effects (low systemic adsorption of the therapeutic agent).

In some embodiments, the formulations described herein provide a mean change from baseline in Target Area Hair Count equal to or higher than 8 hairs/cm² after 6 months of daily or BID application.

In other embodiments, the formulations described herein provide a mean change from baseline in Target Area Hair Count equal to or higher than 9 hairs/cm² after 6 months of daily or BID application.

In other embodiments, the formulations described herein provide a mean change from baseline in Target Area Hair Count equal to or higher than 10 hairs/cm² after 6 months of daily or BID application.

In other embodiments, the formulations described herein provide a mean change from baseline in Target Area Hair Count equal to or higher than 11 hairs/cm² after 6 months of daily or BID application.

In other embodiments, the formulations described herein provide a mean change from baseline in Target Area Hair Count equal to or higher than 12 hairs/cm² after 6 months of daily or BID application.

In some embodiments, the formulations described herein provide a weighted average HGA score equal to or higher than 0.20 after 6 months of daily or BID application.

In other embodiments, the formulations described herein provide a weighted average HGA score equal to or higher than 0.30 after 6 months of daily or BID application.

In some embodiments, the formulations described herein provide a weighted average HGA score equal to or higher than 0.40 after 6 months of daily or BID application.

In some embodiments, the formulations described herein provide a weighted average IGA score equal to or higher than 0.10 after 6 months of daily or BID application.

In other embodiments, the formulations described herein provide a weighted average IGA score equal to or higher than 0.20 after 6 months of daily or BID application.

In other embodiments, the formulations described herein provide a weighted average IGA score equal to or higher than 0.30 after 6 months of daily or BID application.

In some embodiments, the formulations described herein provide a favorable (positive) HGA score in at least about 10% of subjects after 6 months of daily or BID application.

In other embodiments, the formulations described herein provide a favorable (positive) HGA score in at least about 20% of subjects after 6 months of daily or BID application.

In other embodiments, the formulations described herein provide a favorable (positive) HGA score in at least about 30% of subjects after 6 months of daily or BID application.

In some embodiments, the formulations described herein provide a favorable (positive) IGA score in at least about 10% of subjects after 6 months of daily or BID application.

In other embodiments, the formulations described herein provide a favorable (positive) IGA score in at least about 20% of subjects after 6 months of daily or BID application.

In other embodiments, the formulations described herein provide a favorable (positive) IGA score in at least about 30% of subjects after 6 months of daily or BID application.

In other embodiments, the formulations described herein provide a favorable (positive) IGA score in at least about 40% of subjects after 6 months of daily or BID application.

In some embodiments, the formulations described herein are effective in stimulating the hair re-growth, providing the TAHC, HGA scores and IGA scores above disclosed, without exerting a systemic antiandrogenic activity. Such formulations are devoid of side effects attributable to systemic antiandrogenic effects. Said side effects include, but are not limited to, decreased libido, erectile dysfunction (impotence), ejaculation disorders, and decreased volume of ejaculate.

Storage Stability

Storage stability is an important metric for pharmaceutical products. In general, greater stability means that a given formulation is both easier to transport and store, increasing the likelihood that it will be stocked by pharmacies and that patients will not have to be concerned with special storage instructions. The formulations described herein have a desirable stability profile allowing for storage of the final formulation for at least about 3 months, at least about 6 months, at least about 9 months, at least about 12 months, at least about 15 months, at least about 18 months, at least about 21 months, or at least about two years—each at room or refrigerated temperatures.

For example, one of the main degradation pathways of cortexolone-17α-propionate is transesterification to cortexolone-21-propionate (17a-hydroxy-21-propionyloxy-pregna-4-ene-3,20-dione):

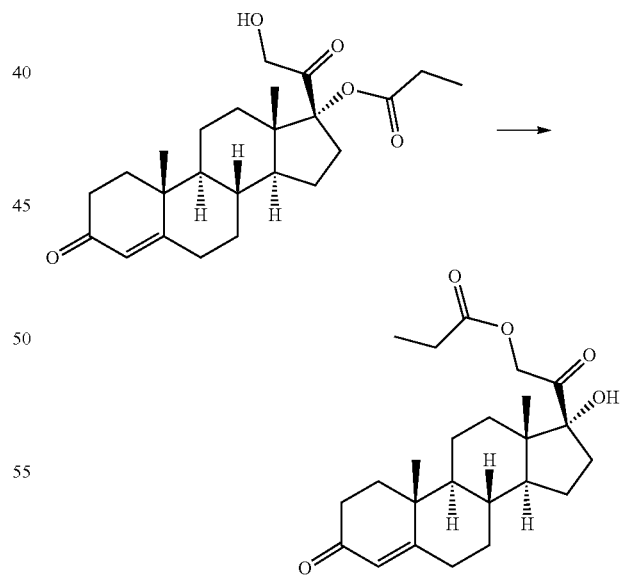

It has now been surprisingly discovered that by maintaining the formulations disclosed herein at a pH of less than about 6, and in certain embodiments, less than about 5, between about 4 and about 5, or at about 4, this degradation process can be dramatically slowed. In particular embodiments, the pH can be 4. The appropriate pH can be obtained via addition of a suitable amount of a pH modifier.

Acceptable pH modifiers include those pharmaceutically acceptable organic and inorganic acids known to those of ordinary skill in the art. Examples of such acids, include, but are not limited to 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; L-ascorbic acid; L-aspartic acid; benzenesulfonic acid; benzoic acid; (+)-camphoric acid; (+)-camphor-10-sulfonic acid; capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; D-glucoheptonic acid; D-gluconic acid; D-glucuronic acid; glutamic acid; glutaric acid; glycerophosphoric acid; glycolic acid; hippuric acid; hydrobromic acid; hydrochloric acid; isobutyric acid; lactic acid; lactobionic acid; lauric acid; maleic acid; L-malic acid; malonic acid; mandelic acid; methanesulfonic acid; naphthalene-1,5-disulfonic acid; naphthalene-2-sulfonic acid; nicotinic acid; nitric acid; oleic acid; oxalic acid; palmitic acid; pamoic acid; phosphoric acid; proprionic acid; L-pyroglutamic acid; salicylic acid; sebacic acid; stearic acid; succinic acid; sulfuric acid; L-tartaric acid; thiocyanic acid; p-toluenesulfonic acid; and undecylenic acid. In particular embodiments, the pH modifying agent can be citric acid.

In certain embodiments, the formulations described herein can, at room or refrigerated temperatures, have less than about 5 weight percent cortexolone-21-propionate or other degradation product after storage for a period of about 24 months.

While pH can be important to stability, it has also been discovered that addition of an antioxidant to the formulation can assist in maintaining storage stability. The antioxidant can be present in addition to a pH modifier. But in some embodiments, the pH modifier can be substantially or completely absent. The antioxidant can be present in the amounts specified elsewhere herein.

It has surprisingly found that a formulation containing cortexolone-17α-propionate as disclosed herein provides acceptable pharmacokinetics profiles of both cortexolone 17α-propionate and/or its metabolites, providing a therapeutically effective amount of the therapeutic agent to the scalp and/or skin while minimizing systemic exposure. Without wishing to be bound to a particular theory, it is believed that the formulations disclosed herein deliver the therapeutic agent to the derma, with deeper penetration minimized by the nature of the formulations disclosed herein. This effect is evidenced in Franz cell data reported in Examples 6 and 7, below.

Thanks to such a favorable pharmacokinetic profile, with high therapeutic levels of the therapeutic agent at the target site and low levels in the systemic circulation, the formulation as disclosed herein is efficacious for treating alopecia, without significant adverse events.

In addition, the formulation herein disclosed has an optimal stability profile allowing a storage of the final product for at least two years (upon storage at refrigerated or room temperature, as defined by Pharmaceutical Guidelines).

EXAMPLES

The formulations described herein are now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Example 1: Evaluation of Cortexolone-17α-Propionate Solubility 5 g of cortexolone-17α-propionate was added to 100 ml of each of the solvents or solvent mixtures shown in Table 1, below, in an effort to produce a 5% w/v solution of cortexolone-17α-propionate. In the examples in Table 1, ethanol refers to ethanol 96°.

TABLE 1

| Solvent (v:v) | Cortexolone-17α-propionate Solubility at Room Temperature |
|---|---|
| Water | Insoluble |
| Ethanol | Highly soluble |
| TRANSCUTOL ® | Very soluble |
| Propylene glycol | Sparingly soluble |
| Isopropyl myristate | Insoluble |
| Isopropyl palmitate, | Insoluble |
| Caprylocaproyl polyoxyl-8 glycerides NF (LABRASOL ®) | Sparingly soluble |
| TRANSCUTOL ®/water (1:1) | Insoluble |
| TRANSCUTOL ®/water/ethanol (1:1:1) | Soluble |
| Ethanol/propylene glycol (1:1) | Soluble |
| Ethanol/propylene glycol/ TRANSCUTOL ® (1:1:1) | Very soluble |
| Water/propylene glycol/ TRANSCUTOL ® (1:1:1) | Insoluble |
| Water/propylene glycol/ TRANSCUTOL ® (1:1:2) | Soluble |

As can be seen from the data in Table 1, water is an unsuitable solvent for cortexolone-17α-propionate when used alone or in a binary mixture. TRANSCUTOL® increased solubility of the therapeutic agent in each mixture in which it was used. Ethanol was likewise found to readily solubilize cortexolone-17α-propionate, but cannot be used alone due to possible burning after topical application as well its potential for abuse.

Example 2: Evaluation of pH on Cortexolone-17α-Propionate Stability

In a suitable container, under stirring, 50 g of cortexolone-17α-propionate was dissolved in a mixture of TRANSCUTOL® (461 g) and ethanol 96° (200 g). After complete dissolution of the cortexolone-17α-propionate, water (283 g) was added slowly. Finally, polysorbate 80 (5 g) and Alpha tocopherols (Vitamin E) (1 g) were added to the formulation. The natural pH of this formulation was measured using a standard pH electrode to be about 5.1.

The formulation was then split into three equal batches, each weighing about 300 g. Citric acid was added to the first batch to lower the pH to about 4. Sodium citrate was added the second batch to increase the pH to about 6. The third batch, having a natural pH of about 5.1, was used as a control. The three batches were then subjected to a short term stability study at 30° C., with the results shown in Table 2.

TABLE 2

| | | Cortexolone-21-propionate Contents* | | |
|---|---|---|---|---|
| PH | Time 0 | After 1 month (30° C.) | After 2 months (30° C.) | After 3 months (30° C.) |
| 4 | 0.04% | 0.16% | 0.26% | 0.37% |
| 5.1 | 0.68% | 1.48% | 1.85% | 1.80% |
| 6 | 10.79% | NA | NA | NA |

*Cortexolone-21-propionate contents calculated as (% (w/w) of cortexolone-21-propionate)/(% (w/w) of cortexolone-17α-propionate × 100)

The above data clearly shows that production of cortexolone-21-propionate is significantly lowered at a pH of about 4.

Example 3: Antioxidant Evaluation

To a formulation containing 5 weight percent cortexolone-17α-propionate in a mixture of TRANSCUTOL®, propylene glycol, and ethanol (96°) in ratio of about 1:1:1 by weight, and further containing polysorbate 80 at 0.1 weight percent, the following antioxidants were added: Alpha tocopherols (Vitamin E) 0.3 weight percent; butylated hydroxyanisole (BHA) 0.01 weight percent, or ascorbyl palmitate 0.5 weight percent. The three formulations were then studied under short term stability conditions. The results are shown in Table 3.

TABLE 3

| | Total Impurities Contents (Impurity percent = (sum of the % (w/w) of each impurity)/% (w/w) of cortexolone 17-alpha propionate * 100) | | | |
|---|---|---|---|---|
| Antioxidant | Time 0 | After 1 month (30° C.) | After 2 months (30° C.) | After 3 months (30° C.) |
| Alpha tocopherols (Vitamin E) | 0.62% | 1.33% | 1.56% | 1.78% |
| BHA | 1.37% | 2.86% | 2.57% | NA |
| Ascorbyl palmitate | 0.05% | 0.22% | 0.29% | 0.37% |

Ascorbyl palmitate provided the least amount of total degradation products.

Example 4a: Anhydrous 5% w/w Solution

A 5 weight percent (w/w) solution of cortexolone-17α-propionate having the components shown in Table 4, below, was prepared by solubilizing the therapeutic agent in the mixture of solvents followed by the addition of the antioxidant (ascorbyl palmitate) and the emulsifier (polysorbate 80).

TABLE 4

| Component | Amount (g/100 g) | Amount (Kg/15 Kg batch) |
|---|---|---|
| Cortexolone-17α-propionate | 5.00 | 0.75 |
| Diethylene glycol monoethyl ether | 31.50 | 4.725 |
| Alcohol (Ethanol) | 31.50 | 4.725 |
| Ascorbyl palmitate | 0.50 | 0.075 |
| Polysorbate 80 | 0.10 | 0.015 |
| Propylene glycol | 31.40 | 4.710 |

This formulation provided the stability profile (40° C./75% RH) shown in Table 5.

TABLE 5

| Time point | Cortexolone-17α-propionate (% w/w) | Cortexolone 21-propionate %* | Total impurities %* |
|---|---|---|---|
| 0 | 5.108 | 0.07 | 0.13 |
| 1 month | 5.046 | 1.08 | 1.19 |
| 3 months | 4.989 | 2.78 | 3.11 |
| 6 months | 4.847 | 4.76 | 5.23 |

*Percentages of cortexolone-21-propionate and total impurities calculated as noted in Examples 2 and 3.

Example 4b: Anhydrous 5% w/v Solution

A 5% (w/v) solution of cortexolone-17α-propionate having the components shown in Table 6, below, was prepared by solubilizing the therapeutic agent in the mixture of solvents followed by the addition of the antioxidant (ascorbyl palmitate) and the emulsifier (polysorbate 80).

TABLE 6

| Component | Amount (g/100 mL) | Amount (Kg/20 L batch) | Amount (Kg/50 L batch) |
|---|---|---|---|
| Cortexolone-17α-propionate | 5.000 | 1.000 | 2.500 |
| Diethylene glycol monoethyl ether (TRANSCUTOL®) | 30.000 | 6.000 | 15.000 |
| Alcohol (Ethanol) | 30.000 | 6.000 | 15.000 |
| Ascorbyl palmitate | 0.500 | 0.100 | 0.250 |
| Polysorbate 80 | 0.100 | 0.020 | 0.050 |
| Propylene glycol | Q.s. to 100 mL | Q.s. to 20 L | Q.s. to 50 L |

Example 5: Aqueous 5% w/w Solution

A formulation of cortexolone-17α-propionate having the components shown in Table 7, below, was prepared by solubilizing the therapeutic agent in the mixture of solvents followed by the addition of the antioxidant and the emulsifier.

TABLE 7

| Component | Amount (g/100 g) | Amount (Kg/15 Kg batch) |
|---|---|---|
| Cortexolone-17α-propionate | 5.00 | 0.750 |
| TRANSCUTOL® | 46.10 | 6.915 |
| Purified water | 28.30 | 4.245 |
| Ethanol | 20.00 | 3.00 |
| Polysorbate 80 | 0.50 | 0.075 |
| Alpha tocopherols (vitamin E) | 0.10 | 0.015 |
| Citric acid, monohydrate | Q.s. to bring the pH to 4.0-4.5 | Q.s. to bring the pH to 4.0-4.5 |

The stability of this formulation at 40° C./75% RH is shown in Table 8.

TABLE 8

| Time point | Cortexolone-17α-propionate (% W/W) | Cortexolone 21-propionate % | Total impurities % |
|---|---|---|---|
| 0 | 5.127 | 0.08 | 0.14 |
| 1 month | 5.064 | 1.19 | 1.38 |
| 3 months | 4.962 | 3.79 | 4.21 |
| 6 months | 4.546 | 7.66 | 8.41 |

Based on the impurity profile, the formulation prepared in Example 4a is more stable than the aqueous formulation of Example 5.

Example 6: Clinical Evaluation

The formulation described in Example 4b was studied in a clinical trial to evaluate its pharmacokinetic profile, safety, and tolerability. According to the study protocol, 1 ml of the formulation (corresponding to 50 mg of cortexolone-17α-propionate) was applied once a day on study day 1 and then twice daily thereafter on study days 2-28 to the areas of the scalp suffering from alopecia. The formulation provided the pharmacokinetic profile shown in Tables 9 and 10 and the excretion data shown in Table 11. Statistical analyses were performed using SAS® version 9.1.3, service pack 4 for Windows and Phoenix WinNonLin 6.3, Pharsight Corporation, USA.

TABLE 9

PK parameters after single dose administration

|  | $C_{max}$ (ng/ml) (N = 18) | $T_{max}$ (h) (N = 18) | $AUC_{0-t}$ (ng*h)/ml (N = 18) |
| --- | --- | --- | --- |
| Mean (±SD) | 1.04 ± 0.41 | 6.22 ± 5.17 | 15.69 ± 4.30 |
| Median | 0.98 | 4.0 (4-24) | 15.26 |
| (range) | (0.57-1.96) |  | (9.47-24.53) |

TABLE 10

PK parameters after repeated dose administration (steady state)

|  | $C_{max}$ (ng/ml) (N = 17) | $T_{max}$ (h) (N = 17) | $AUC_t$ (ng*h)/ml (N = 17) | $T_{1/2}$ (h) (N = 16) |
| --- | --- | --- | --- | --- |
| Mean (±SD) | 3.82 ± 1.34 | 4.38 ± 1.96 | 37.37 ± 12.36 | 17.84 ± 9.12 |
| Median | 4.03 | 4.0 (0.5-8) | 37.71 | 14.84 |
| (range) | (1.77-7.04) |  | (18.39-64.11) | (7.93-47.73) |

TABLE 11

Excretion parameters at 1st and 55th application

| | Application | | | |
| --- | --- | --- | --- | --- |
| | 1st Application (Day 1) (N = 18) | | 55th Application (Day 28) (N = 17) | |
| Parameter | Total | Free | Total | Free |
| | Cortexolone-17α-propionate | | | |
| Analyte Excreted (μg) | 126.37 ± 48.99 | 0.16 ± 0.34 | 429.53 ± 178.24 | 2.72 ± 1.54 |
| % Excreted | 0.25 ± 0.10 | 0 ± 0 | | |
| | Cortexolone | | | |
| Analyte Excreted (μg) | 0.06 ± 0.26 | BLQL | 0.64 ± 0.74 | BLQL |
| | Tetrahydrocortexolone | | | |
| Analyte Excreted (μg) | 71.45 ± 21.36 | BLQL | 226.03 ± 100.10 | 0.46 ± 0.65 |

Example 7: Franz Cell Diffusion Test 1

In an in vitro study, the skin penetration potential of cortexolone-17α-propionate was compared to cyproterone acetate using a standard Franz cell. According to the protocol, 300 mg of each test formulations was applied as saturated solution with a concentration ranging from 0.7 to 1 weight (w/w) to 2.54 cm² of exposed skin area. The receptor chamber volume ranged from 4.75 ml to 6.4 ml of phosphate buffered saline/fetal calf serum (2:1) containing penicillin/streptomycin according to standard protocol, and was maintained at a temperature of 32° C.+/−1° C. Stirring was maintained at 300 rpm.

The experiments were conducted for 48 h in triplicate. 100 μl fractions were withdrawn at 5-7 time points during the 48 h test period. After withdrawing a 100 μl fraction for analysis, it was replaced with fresh receiver fluid in an equal volume. At the end of the experiment, the skin was taken from the Franz cells and the skin's stratum corneum was removed by tape stripping (20×) with transparent adhesive tape (Koren, Spain).

The strippings were analyzed by dissolution in a mixture of propylene glycol:oleyl alcohol 9:1. The resulting mixture was analyzed for concentration of cyproterone acetate and cortexolone-17α-propionate, with the results provided in Table 12, below.

TABLE 12

| Compound | Applied Concentration [%] | Skin concentration [μg/g] | Permeation rate [ng/ml/h] |
| --- | --- | --- | --- |
| Cyproterone Acetate | 0.94 | 89.4 ± 4.6 | 141 ± 17 |
| Cortexolone-17α-propionate | 0.99 | 231 ± 19 | 1410 ± 137 |

As can be seen from the data, cortexolone-17α-propionate permeates skin about 3 times as much as cyproterone acetate and has a permeation rate that is about 10 times greater than cyproterone acetate.

Example 8: Franz Cell Diffusion Test 2

Concentration of the active agent in the receiver fluid was measured next using a system largely identical to the system in Example 7. 3 human donor skin samples were used and the permeation, expressed as Cumulative Permeated amount (μg/cm²), is shown in Table 13. This experiment compared the anhydrous solution of Example 4a and the aqueous solutions of Example 5. Each contained the same amount of cortexolone-17α-propionate (5%).

TABLE 13

| Time [h] | Anhydrous solution of Ex. 4a | Aqueous solution of Ex. 5 |
| --- | --- | --- |
| 5 | 0.862 | 0.94 |
| 7 | 2.75 | 1.36 |
| 9 | 6.36 | 1.97 |
| 24 | 38.1 | 12.5 |
| 26 | 45.7 | 14.9 |
| 28 | 55.7 | 19.6 |

As is evident from the data in Table 13, water in the formulation can reduce cortexolone-17α-propionate's penetration into the skin.

Example 9: Phase 2 Clinical Study in Males with Androgenetic Alopecia (AGA)

The formulation described in Example 4b was studied in a multicenter, randomized, double-blind, phase 2 controlled study. In the study, the formulation of Example 4b (cortexolone-17α-propionate solution 5%) was compared to vehicle solution as placebo. Both the formulation containing the active and the vehicle formulation were applied twice-daily for 26 weeks in males with androgenetic alopecia (AGA). The study was compliant with Good Clinical Practices (GCP) for Clinical Research Studies.

Objective

The primary objective of this study was to compare the safety and efficacy of topical application of cortexolone-17α-propionate 5% solution (having the composition of Example 4b) (twice a day) and the vehicle solution (twice a day) in males with AGA.

Study Subjects

The subjects were 18 to 50 years of age and had mild to moderate AGA at the temple and vertex regions of the scalp, with a modified Hamilton-Norwood Scale rating of III vertex to V (IIIv, IV, V), and ongoing hair loss.

Treatment

Subjects received either cortexolone-17α-propionate 5% solution or vehicle control solution depending on the allocation group and applied the provided formulation to the balding areas of the scalp (vertex and temple) twice a day for 6 months.

Visits Schedule

Subjects had visits at baseline (visit 2), $1^{st}$ month (visit 3), $2^{nd}$ month (visit 4), $4^{th}$ month (visit 5) and $6^{th}$ month (visit 6). Subject screening (visit 1) took place within 2 weeks of baseline visit (Visit 2). In all the study visits, all measurements for efficacy and safety endpoints were performed, with the exception of visits 2 and 3, where only local tolerability assessment (LTA) and adverse events (AEs) evaluation were performed.

Study Measurements

In Table 14, the study measurements for hair loss classification, efficacy endpoints and safety endpoints are reported.

TABLE 14

| Study measurements | |
| --- | --- |
| Type of assessment | Study measurements |
| Hair loss classification | The modified Norwood-Hamilton Scale was used to assess the eligibility of subjects at the Screening Visit. Subject had to have mild to moderate AGA in temple and vertex region rating Modified Hamilton-Norwood Scale III vertex to V (IIIv, IV, V) with ongoing hair loss to be eligible for this study. |
| Efficacy | Standardized macro photography to assess Target Area Hair counts (TAHC) was performed at months 2, 4, and 6. Standardized global photography (for Subject Self-Assessment and Investigator Global Assessment) was preformed at screening and months 2, 4, and 6. Subject Self-Assessments (SSA) Questionnaires were completed by the subject at months 2,4, and 6. The subject used the baseline standardized global photo of their scalp and compared it, side by side, with a "real time" standardized global photo from the current visit to provide a comparative assessment for Hair Growth Assessment (HGA), Hair Growth Index (HGI), and Hair Growth Satisfaction Scale (HGSS). 1. HGA-Scalp hair growth was compared from baseline using the following 7-point scale: greatly decreased (−3), moderately decreased (−2), slightly decreased (−1), no change (0), slightly increased (1), moderately increased (2), and greatly increased (3). 2. HGI-Hair growth was compared from baseline by three questions on a health outcome questionnaire: [1] "Since the start of treatment, when I look at my thinning area, I can see . . . (scalp)", [2] "Since the start of treatment, my hair now covers . . . (scalp)", and [3] "Since the start of treatment, the appearance (thickness/quality/amount) of the thinning area on my head is . . . "; were scored using the following 7-point scale: much less (−3), moderately less (−2), slightly less (−1), the same amount (0), slightly more (1), moderately more (2), much more (3). 3. HGSS-Hair appearance/growth was compared from baseline by five questions: How satisfied do you feel about: [1] The overall appearance by your hair; [2] The appearance of the thinning area(s) within treatment areas on your head; [3] The amount of scalp that can be seen in the treatment areas; [4] The amount of hair in the treatment areas; [5] The growth of hair in the treatment areas; were scored using the following |

TABLE 14-continued

Study measurements

| Type of assessment | Study measurements |
|---|---|
| | 7-point scale: very dissatisfied (−3), dissatisfied (−2), somewhat dissatisfied (−1), neutral/neither satisfied nor dissatisfied (0), somewhat satisfied (1), satisfied (2), very satisfied (3). Investigator Global Assessment (IGA) measuring change in scalp hair growth. The evaluator used a standardized global photo (see above) of the subject's scalp taken at baseline and compared it with the clinic visit's live-assessment of the subject's scalp hair growth using a 7-point scale: greatly decreased (−3), moderately decreased (−2), slightly decreased (−1), no change (0), slightly increased (1), moderately increased (2), and greatly increased (3). |
| Safety | Local and systemic adverse events (AEs) were assessed at each visit. Local tolerability assessment (LTA) of erythema, scaling, pruritus, and burning/stinging were graded on discrete 5-point scale: none (0), minimal (1), mild (2), moderate (3), and severe (4) and performed at Baseline, and Months 1, 2, 4, and 6. In addition, the investigator assessed reactions known to be associated with topical application of steriods including skin atrophy, telangiectasia, folliculitis, hypopigmentation, and hyperpigmentation graded on discrete 5-point scale: none (0), trace (1), mild (2), moderate (3), severe (4). |

In Table 15, the study endpoints, categorized as efficacy or safety endpoints, are reported.

TABLE 15

Study endpoints.

| Type of endpoints | Endpoints |
|---|---|
| Efficacy | Primary endpoints:<br>1. Changes from Baseline in Target Area Hair Counts (TAHC) [in number of non-vellus hairs] using digital image analysis at Month 6.<br>2. The subject's evaluation of treatment benefit via the Hair Growth Assessment (HGA) question at Month 6.<br>Secondary endpoints:<br>1. The subject's evaluation of treatment benefit via the Hair Growth Index (HGI) and Hair Growth Satisfaction Scale (HGSS) questionnaires at Month 6.<br>2. Investigator Global Assessment (IGA) at Month 6. |
| Safety | 1. Local tolerability.<br>2. Local and systemic AEs. |

The Intent-To-Treat (ITT) population included all randomized subjects, that received at least one application of the study drug, and was the primary population used for safety assessment. The per-protocol (PP) population was the subset of the ITT population completing the study and without major protocol deviations, and was considered as the primary population for statistical analysis of efficacy endpoints. At the end of the study, the ITT was subdivided in the study groups as follows: 31 subjects in cortexolone-17α-propionate solution 5% arm and 33 subjects in vehicle solution arm. At the end of the study, the PP population was subdivided in the study groups as follows: 23 subjects in cortexolone-17α-propionate solution 5% arm and 25 subjects in vehicle solution arm.

Changes from Baseline in Non-Vellus Target Area Hair Count (TAHC) at Month 6 (Primary Efficacy Endpoint)

Non-vellus Target Area Hair Count (TAHC) was calculated using digital image analysis from standardized macro photographs collected at month 2, 4 and 6. Table 16 reports the change from baseline in non-vellus TAHC at month 6 for the PP population: the values refer to the change, from baseline, in the number of non-vellus hairs in a 1 $cm^2$ area of the scalp after 6 months of treatment.

TABLE 16

Change from Baseline in Non-Vellus TAHC at Month 6.

| Change from Baseline in Non-Vellus TAHC at Month 6 (Area: 1 $cm^2$) | Cortexolone-17α-propionate solution 5% (Example 4b) n | Vehicle |
|---|---|---|
| PP Population | | |
| N | 23 | 25 |
| Mean | 12.7 | 2.9 |
| Median | 13.0 | 1.0 |
| Standard Deviation | 32.94 | 18.08 |
| Minimum, Maximum | −66.0, 86.0 | −26.0, 50.0 |

As is demonstrated in the data above, cortexolone-17α-propionate solution (5%) had larger changes from baseline in non-vellus TAHC compared to vehicle at month 6. Cortexolone-17α-propionate solution 5% (according to Example 4b) had a larger mean change from baseline in non-vellus TAHC (12.7) with respect to vehicle, which had a mean change from Baseline in non-vellus TAHC of 2.9.

Hair Growth Assessment at Month 6

Subjects used the baseline standardized global photo of their scalp and compared it, side by side, with a "real time" standardized global photo at month 6 to provide a comparative assessment for HGA. Subjects evaluated hair growth using a 7-point scale. FIG. 1 depicts HGA frequency distribution for the two treatment groups at month 6. In the figure, negative HGA scores (−3, −2 and −1) have been grouped into a global HGA score named "unfavorable"; score 0 is named "no change," and positive scores (+1, +2 and +3) have been grouped into a global HGA score named "favorable". HGA scores for the PP population at month 6 are reported in Table 17.

TABLE 17

HGA scores for PP population at month 6.

| HGA score | Cortexolone-17α-propionate solution 5% (Example 4b) Nr. of subjects (%) | Vehicle Nr. of subjects (%) |
|---|---|---|
| +3 | 1 (4.3%) | 0 (0.0%) |
| +2 | 3 (13.0%) | 2 (8.0%) |
| +1 | 5 (21.7%) | 2 (8.0%) |
| 0 | 8 (34.8%) | 11 (44.0%) |
| −1 | 5 (21.7%) | 8 (32.0%) |
| −2 | 1 (4.3%) | 2 (8.0%) |
| −3 | 0 (0.0%) | 0 (0.0%) |

The proportion of subjects who rated scalp hair growth as favorable was directionally larger in cortexolone-17α-propionate solution 5% (39%) compared to vehicle (16%). Of those subjects with favorable hair growth, the proportion of subjects who rated hair growth as greatly increased (+3), moderately increased (+2), and slightly increased (+1) was 4%, 13%, and 22%, respectively for cortexolone-17α-propionate solution 5%, and 0%, 8%, and 8% respectively, for vehicle. The weighted average of HGA at month 6 for both the treatment groups (PP populations) was calculated: cortexolone-17α-propionate solution 5% had a higher HGA weighted average at month 6 (0.30) compared to placebo (−0.24).

This data demonstrates that subjects in the cortexolone-17α-propionate solution 5% group had a larger magnitude of improvement compared to vehicle solution.

Hair Growth Index (HGI) at Month 6

Subjects used the baseline standardized global photo of their scalp and compared it, side by side, with a "real time" standardized global photo at month 6 to provide a comparative assessment for HGI. Hair growth was compared from baseline by three questions on a health outcome questionnaire. The proportion of subjects who rated scalp hair growth as favorable was larger in cortexolone-17α-propionate solution 5% (Q1: 39%, Q2: 35%, and Q3: 43%) compared to vehicle (Q1: 16%, Q2: 12%, and Q3: 20%).

Hair Growth Satisfaction Scale (HGSS) at Month 6

Subjects used the baseline standardized global photo of their scalp and compared it, side by side, with a "real time" standardized global photo at month 6 to provide a comparative assessment for HGSS. Hair appearance/growth was compared from baseline using five questions. The proportion of subjects who were satisfied with scalp hair growth was larger in cortexolone-17α-propionate solution 5% compared to vehicle solution. For questions #1-5 (Q1-Q5), the proportion of subjects who rated scalp hair growth as favorable (scores of +1, +2 and +3) was higher for cortexolone-17α-propionate solution 5% (Q1: 38%, Q2-Q5: 30%) compared to vehicle solution (Q1/Q3: 8%, Q2/Q4/Q5: 20%). For cortexolone-17α-propionate 5% solution, no subjects were 'very dissatisfied' (score of −3) for any of the HGSS questions at Month 6, whereas, for vehicle, there were some subjects very dissatisfied in all the HGSS questions at month 6.

Investigator's Global Assessment (IGA) at Month 6

Figure 2:
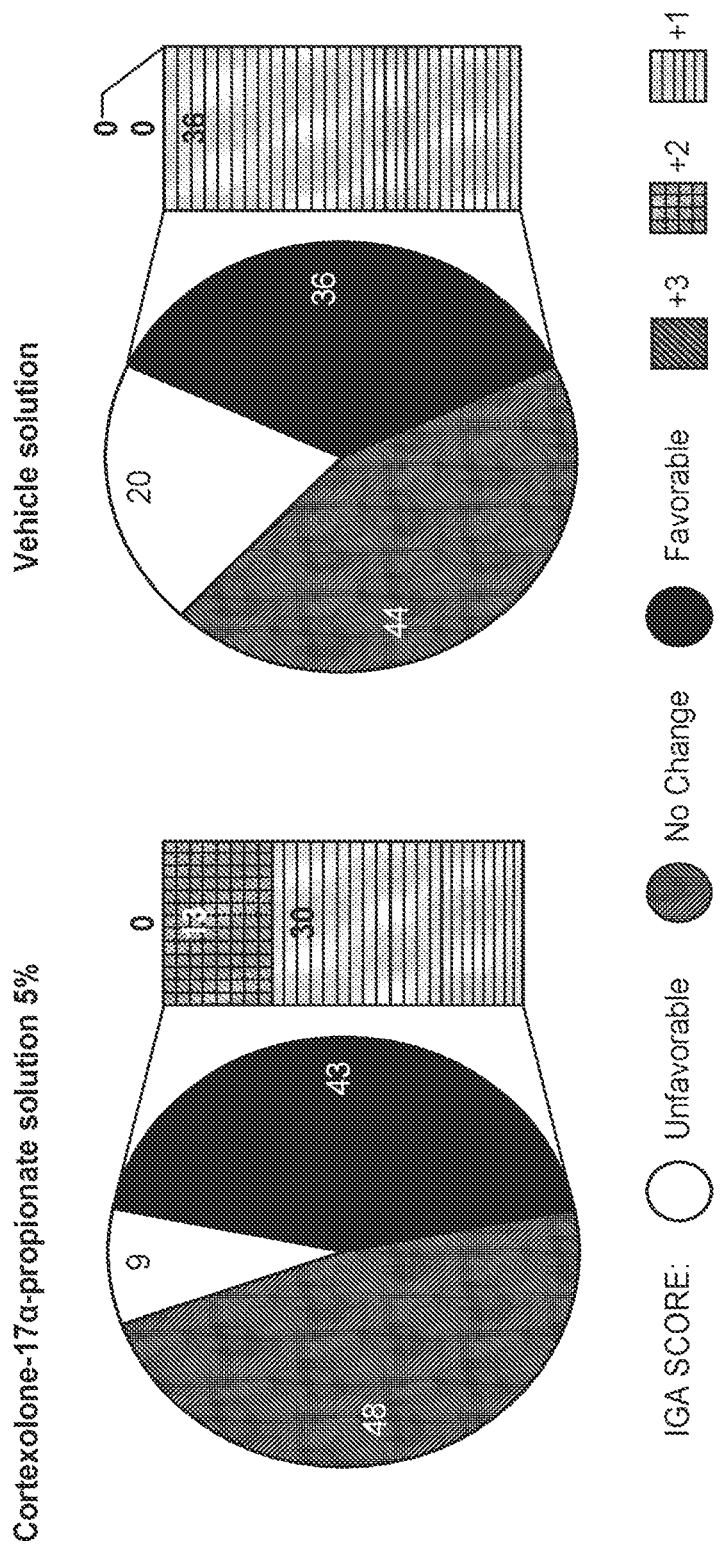
FIG. 2 depicts the frequency distribution of Investigator's Global Assessment (IGA) for hair growth in two treatment groups after 6 months of treatment in the Phase 2 clinical study in males with AGA described in Example 9.

At month 6, investigators used a standardized global photo of the subject's scalp taken at baseline and compared it with a live-assessment of the subject's scalp hair growth using a 7-point scale. FIG. 2 depicts the frequency distribution of IGA for two treatment groups (one for cortexolone-17α-propionate solution and one for vehicle solution) at month 6. In FIG. 2, negative IGA scores (−3, −2 and −1) are grouped into a global IGA score named "unfavorable"; score 0 is named "no change" and positive scores (+1, +2 and +3) are grouped into a global IGA score named "favorable". IGA scores for the PP population at month 6 are reported in Table 18.

TABLE 18

IGA scores for PP population at month 6.

| IGA score | Cortexolone-17α-propionate solution 5% (Example 4b) Nr. of subjects (%) | Vehicle Nr. of subjects (%) |
|---|---|---|
| +3 | 0 (0.0%) | 0 (0.0%) |
| +2 | 3 (13.0%) | 0 (0.0%) |
| +1 | 7 (30.4%) | 9 (36.0%) |
| 0 | 11 (47.8%) | 11 (44.0%) |
| −1 | 1 (4.3%) | 4 (16.0%) |
| −2 | 1 (4.3%) | 1 (4.0%) |
| −3 | 0 (0.0%) | 0 (0.0%) |

The proportion of subjects who had a favorable IGA score (scores of +1, +2 and +3) was higher in the cortexolone-17α-propionate solution 5% group (43%) than in the vehicle group (36%), and the proportion of subjects who had an unfavorable IGA score (scores of −1, −2 and −3) was lower for cortexolone-17α-propionate (9%) compared to the vehicle (20%). The weighted average of IGA at month 6 for both the treatment groups (PP populations) was calculated: cortexolone-17α-propionate solution 5% had a higher IGA weighted average at month 6 (0.43) compared to placebo (0.12).

This data demonstrates that subjects in the cortexolone-17α-propionate solution 5% group had a larger magnitude of improvement compared to the vehicle solution.

Local Tolerability and Adverse Events Assessment

Local Tolerability Assessment analysis was performed on all subjects that applied the test article at least once (ITT population). The incidence of each sign in the LTA was low throughout the study and generally similar among the treatment groups. Of the local tolerability signs reported, most signs were minimal to mild in severity, with (in descending order of incidence) pruritus, scaling, erythema, folliculitis, hyperpigmentation, and hypopigmentation present after treatment.

The incidence of Adverse Events (AEs) was similar among the treatment groups, with most events typically mild in severity and not related to the test article. In the cortexolone-17α-propionate solution 5% group, AEs occurred in 18/31 subjects (58.1%), while, in the vehicle group, AEs occurred in 17/33 subjects (51.5%). The majority of AEs were mild. 4 AEs in vehicle group were rated as severe, with only one of them (headache) possibly related to the test article. No severe AE in cortexolone-17α-propionate group occurred.

Importantly, no adverse events which could be due to a systemic antiandrogenic effect (e.g. decreased libido, erectile dysfunction, and/or ejaculation disorder) occurred in any of the patients treated with cortexolone-17α-propionate solution 5% for 6 months.

Conclusions

The study was a Phase II POC study in a limited number of subjects, and was not powered to show statistically significant differences among study groups; nevertheless, the study demonstrated a superior improvement in hair growth of cortexolone 17α-propionate solution 5% compared to vehicle: at month 6, in the PP population, cortexolone 17α-propionate (12.7) had superior change from Baseline in non-vellus Target Area Hair Count (TAHC) compared to vehicle (2.9). The result of subject Hair Growth Assessment questionnaire (the other primary efficacy endpoint of the study) was consistent with the quantitative TAHC measurements, and the proportion of subjects who rated scalp hair growth as favorable was larger in cortexolone 17α-propionate (39%) compared to vehicle (16%); of those subjects who rated scalp hair growth as favorable, cortexolone 17α-propionate tended to have a larger magnitude of improvement compared to vehicle. The results of the secondary endpoints were generally consistent with that of the primary endpoints.

Example 10: 15% (w/v) Solution

A 15% (w/v) solution of cortexolone-17α-propionate having the components shown in Table 19, below, was prepared by solubilizing the therapeutic agent in the mixture of solvents followed by the addition of the antioxidant (ascorbyl palmitate) and the emulsifier (polysorbate 80).

TABLE 19

| Component | Amount (g/100 mL) | Amount (Kg/20 L batch) |
| --- | --- | --- |
| Cortexolone-17α-propionate | 15.000 | 3.000 |
| Diethylene glycol monoethyl ether (Transcutol ®) | 28.000 | 5.600 |
| Alcohol (Ethanol) | 28.000 | 5.600 |
| Ascorbyl palmitate | 0.500 | 0.100 |
| Polysorbate 80 | 0.100 | 0.020 |
| Propylene glycol | Q.s. to 100 mL | Q.s. to 20 L |

Example 11: Comparison of the Effects of the Formulation of Example 4b and the Commercially Available Finasteride 1 mg Tablet (PROPECIA®)

Based on the results of finasteride 1 mg tablets (PROPECIA®) described in the two Phase III clinical studies published online by the United States Food and Drug Administration (the FDA), it can be concluded that the mean change from baseline in non-vellus TAHC at month 6 for cortexolone-17α-propionate solution 5% (according to Example 4b), as reported in Example 9, is very similar to the mean change from baseline in non-vellus TAHC at month 6 observed in 2 phase III clinical trials on finasteride 1 mg tablets (tradename Propecia®) per os once daily. Table 20 below reports the change from baseline in TAHC at month 6 in the two finasteride studies (data of active finasteride groups) as described in the NDA for PROPECIA® published online by the FDA:

TABLE 20

Mean change from baseline in TAHC at month 6 in the 2 finasteride phase III clinical studies (data of active finasteride groups are reported) - original data.

| Study | Change from Baseline in non-vellus TAHC at Month 6 (target area: 1-inch diameter circle, corresponding to 5.1 cm$^2$) |
| --- | --- |
| 087 | 69.5 |
| 089 | 58.4 |
| Combined (study 087 + 089) | 62.4 |

In the two finasteride studies, the target area was a 1-inch diameter circle, which corresponds to 5.1 cm$^2$. In order to compare the changes from baseline in TAHC at month 6 obtained in the finasteride studies and the change from baseline in TAHC at month 6 obtained with cortexolone-17α-propionate in the study of the present Example 9 (where the target area was 1 cm$^2$), the original finasteride data have been recalculated to take into account the differences between the total surfaces of the target areas (i.e., the values were divided by 5.1) as shown in Table 21.

TABLE 21

Mean change from baseline in TAHC at month 6 in the 2 finasteride phase III clinical studies (data of active finasteride groups are reported), recalculated over a target area of 1 cm$^2$.

| Study | Change from Baseline in non-vellus TAHC at Month 6, recalculated over a target area of 1 cm$^2$ |
| --- | --- |
| 087 | 13.6 |
| 089 | 11.5 |
| Combined (study 087 + 089) | 12.2 |

Accordingly, the changes from baseline in TAHC at month 6 for finasteride were as follows: 13.6 in study 087, 11.5 in study 089 and 12.2 for the two studies combined. It is apparent that these values are almost identical to the change from baseline in TAHC at month 6, in the PP population, for cortexolone-17α-propionate solution 5% prepared according to Example 4b (12.7). As discussed above, at month 6, the efficacy, measured as hair growth, of finasteride 1 mg tablets given per os once daily and of cortexolone-17α-propionate solution 5% topically administered twice daily on the scalp of the patients are comparable.

The phraseology or terminology herein is for the purpose of description and not of limitation. As such, the terminology and/or phraseology of the present specification should be interpreted by the skilled artisan in light of the teachings and guidance herein.

The breadth and scope of the present invention should not be limited by any of the above-described exemplary embodiments, but should be defined only in accordance with the following claims and their equivalents.

All patents, patent applications, and other references noted or referenced in this application are hereby incorporated by reference in their entirety.

What is claimed:

1. A method of treating androgenetic alopecia, the method comprising topically administering to a subject in need thereof, an effective amount of a pharmaceutical formulation comprising:

a) cortexolone-17α-propionate at a concentration of about 5 weight percent to about 15 weight percent,
b) a pharmaceutically acceptable amount of one or more pharmaceutically acceptable solvents, and
c) less than about 5% water, wherein:

the cortexolone-17α-propionate is fully solubilized in the formulation;

the formulation has a pH between about 4 and about 5; and wherein the formulation has a storage stability of at least about 6 months at room temperature as measured by the formulation comprising less than 5 weight percent of cortexolone-21-propionate (17α-hydroxy-21-propionyloxy-pregna-4-ene-3,20-dione) or other degradation products.

2. The method of claim 1, wherein the formulation has a storage stability is at least about 12 months at room temperature.

3. The method of claim 1, wherein the formulation has a storage stability of at least about 18 months at room temperature.

4. The method of claim 1, wherein the formulation has a storage stability of at least about 21 months at room temperature.

5. The method of claim 1, wherein the formulation has a storage stability of at least about 24 months at room temperature.

6. The method of claim 1, wherein the formulation has a pH of about 4.

7. The method of claim 1, wherein the formulation does not contain cortexolone-21-propionate (17α-hydroxy-21-propionyloxy-pregna-4-ene-3,20-dione).

8. The method of claim 1, wherein the formulation comprises no more than 0.4 weight percent of cortexolone-21-propionate (17α-hydroxy-21-propionyloxy-pregna-4-ene-3,20-dione) after 3 months at 30° C.

9. The method of claim 1, wherein the formulation comprises about 7.5 weight percent cortexolone-17α-propionate.

10. The method of claim 1, wherein the formulation comprises about 5 weight percent cortexolone-17α-propionate.

11. The method of claim 1, wherein the formulation is a liquid.

12. The method of claim 1, wherein the one or more pharmaceutically acceptable solvents are selected from the group consisting of a $C_1$-$C_7$ alcohol, a polyol ether, a polyol, a natural oil, an ester, tricaprylin, a medium-chain triglyceride, a caprylocaproyl-8 glyceride, and combinations thereof.

13. The method of claim 1, wherein formulation is administered at least once daily.

14. The method of claim 1, wherein the formulation is administered twice daily or more.

15. The method of claim 1, wherein from about 0.2 to about 2.0 ml of the formulation are administered during each application.

16. The method of claim 1, wherein the one or more pharmaceutically acceptable solvents are selected from the group consisting ethanol, diethylene glycol monoethyl ether, and propylene glycol, and wherein the pharmaceutical formulation contains less than about 3 percent water.

17. The method of claim 16, wherein the ethanol, diethylene glycol monoethyl ether, and propylene glycol are all present in the formulation and are present in a 1:1:1 ratio on a w/w/w basis.

18. The method of claim 17, wherein the pharmaceutical formulation comprises about 7.5 weight percent cortexolone-17α-propionate.

* * * * *